(12) United States Patent
Ohtsuka

(10) Patent No.: US 7,995,812 B2
(45) Date of Patent: Aug. 9, 2011

(54) X-RAY IMAGE PROCESSING SYSTEM AND METHOD THEREOF

(76) Inventor: Hiroshi Ohtsuka, Suita (JP)

(*) Notice: Subject to any disclaimer, the term of this patent is extended or adjusted under 35 U.S.C. 154(b) by 565 days.

(21) Appl. No.: 11/574,409

(22) PCT Filed: Aug. 30, 2006

(86) PCT No.: PCT/JP2006/317144
§ 371 (c)(1),
(2), (4) Date: Feb. 28, 2007

(87) PCT Pub. No.: WO2007/026787
PCT Pub. Date: Mar. 8, 2007

(65) Prior Publication Data
US 2009/0034685 A1 Feb. 5, 2009

(30) Foreign Application Priority Data
Aug. 31, 2005 (JP) ................... 2005-251557

(51) Int. Cl.
*G06K 9/00* (2006.01)
*G01N 23/06* (2006.01)
(52) U.S. Cl. ........... 382/128; 382/132; 382/254; 378/56
(58) Field of Classification Search .................. 382/154, 382/130–133, 162, 164, 254, 128; 378/168, 378/56; 430/619
See application file for complete search history.

(56) References Cited

U.S. PATENT DOCUMENTS

| 6,097,902 A * | 8/2000 | Blume ................... 396/569 |
| 7,283,654 B2 * | 10/2007 | McLain ................. 382/128 |
| 7,431,497 B2 * | 10/2008 | Lucas et al. ............ 378/168 |
| 2004/0259044 A1 * | 12/2004 | Hunt et al. ............. 430/619 |
| 2006/0072799 A1 * | 4/2006 | McLain ................. 382/128 |

FOREIGN PATENT DOCUMENTS
WO WO96/15479 * 5/1996

* cited by examiner

*Primary Examiner* — Daniel G Mariam
*Assistant Examiner* — Nancy Bitar
(74) *Attorney, Agent, or Firm* — Judge Patent Associates

(57) ABSTRACT

System is provided for having more instinct image of an orthopedics disease and an oral surgery disease by applying a series of image processing on a X-ray image and diagnosing more exactly an orthopedics disease and an oral surgery disease. This system comprising means for capturing simple X-ray image in a computer, applying a contrast process on X-ray image taken in a computer, applying an embossing (raising) process on X-ray image which a contrast process was made or not made on, applying a light irradiation process in the embossed (raising) X-ray image, storing and controlling its data and X-rays image provided by a series of image processing, printing X-rays image provided by a series of processes on the monitor or on the paper.

7 Claims, 28 Drawing Sheets

Side dislocation

Flexure dislocation

Shortening dislocation

Extensional dislocation

Sprain dislocation

X-RAY IMAGE PROCESSING SYSTEM AND METHOD THEREOF

TECHNICAL FIELD

The present invention relates to an image processing system and a method thereof for more precise imaging diagnosis of orthopedic and oral surgery diseases, in which a more distinctive image is obtained by applying a series of image processes using a computer to an X-ray image obtained from a simple X-ray examination executed in medical institutions or the like in order to improve accuracy of the X-ray image. The present invention also belongs to a technique to determine exact treatment measures by improving accuracy in the X-ray image so as to reduce inconsistency with clinical.

BACKGROUND ART

One of radiographic examinations widely used for orthopedic and oral surgery examinations is a simple X-ray examination. X-rays passing through a human body are exposed to an X-ray film, generating a latent image in the X-ray film in proportion to intensity of a passing X-ray amount, in which silver bromide of photosensitive emulsion is converted into metallic silver by a developing process. According to an amount of this metallic silver, a change (shade density) of a blackening degree is obtained to form an X-ray image. The simple X-ray examination as stated above is used most frequently in orthopedic examinations.

DISCLOSURE OF THE INVENTION

The Problem to be Solved through Invention

The simple X-ray examination is realized by exposing a patient with radiation, causing the patient to have a risk of radiation exposure. Moreover, the most important factor to influence accuracy of imaging diagnosis is a skill level of a medical worker in a photographic technique of an X-ray image and a diagnostic reading technique of a photographic image. For example, even if diagnosis is made from imaging findings that a fracture being a representative disease in orthopedics is not observed, there is a case that a peculiar symptom accompanied by a fracture such as sever swelling, localized tenderness and dysfunction is observed in clinical findings. That is, in spite of an actual fracture, there is not a few cases to overlook the fracture in the imaging findings. This is because of the difference in an amount of experience and knowledge owned by a medical worker in the diagnostic reading technique of an X-ray image. Moreover, knowledge and experience of a medical worker are important to determine treatment measures. In the case of having no obvious findings in an X-ray image for a medical worker with less experience, there is not a few cases in which the fracture is overlooked as stated above due to little other determination materials. This is an extremely big issue for a patient and causes an excessive treatment which relates to meaningless extension of a treatment period, thereby resulting in occasional sequelae. There is also a danger that easy diagnosis and treatment cause malpractice depending on a situation.

In order to solve the various kinds of the problems generated by the difference of experience as stated above, technical improvement was achieved in an X-ray photographing apparatus, X-ray film, intensifying screen, and developing process or the like, while various clinical measurements are additionally taken for not only the simple X-ray examination but also development of a more advanced imaging diagnosis apparatus such as an X-ray computed tomography apparatus (X-ray CT) and scintigraphy. However, usage of the advanced imaging diagnosis apparatus such as the X-ray CT causes a large biological and physical burden to a patient, and radiation exposure by the X-ray CT reportedly accounts for 3.2% of cancer incidence ratio in Japan. Furthermore, there is a case that some errors are generated for an image finished by the photographic technique of a medical worker in an MRI, leaving a problem such as generation of errors in accuracy of imaging diagnosis depending on the diagnostic reading technique in the same manner with the simple X-ray examination.

Accordingly, an examination and diagnosis method are desired to minimize a burden to a patient and to acquire an information amount required for diagnosis. The present invention was achieved to solve these problems, in which the image processing is applied to an X-ray image obtained from the simple X-ray examination for accuracy improvement of the imaging diagnosis, so that radiation exposure exceeding the simple X-ray examination is not required for the patient. Moreover, integration with computed radiography (referred to as a CR hereinafter) improves accuracy of the imaging diagnosis in the simple X-ray examination itself which is executed in medical institutions or the like, and substantially reduces biological and physical burden to the patient, thereby an effective clinical operation can be realized.

Under the circumstances as stated above, following patent applications have been filed for an X-ray photographing examination, but the technique of the image processing according to the present invention has not been employed yet therein. (Japan patent publication 2004-199194, 2005-501684)

Method to Solve the Problem

To solve above subject, present invention provides a X-ray image processing system of simple X-ray image diagnosing more exactry an orthopedics disease and an oral surgery disease, comprising means for a series of processing a X-ray image, and a system to be able to have decision of an appropriate treatment policy by reducing the difference finding from X-ray image and clinical decision.

To solve above subject, present invention provides a X-ray image processing system of simple X-ray image diagnosing an orthopedics disease and an oral surgery disease, comprising means for: capturing simple X-ray image in a computer, applying a contrast process on X-ray image taken in a computer, applying an embossing (raising) process on X-ray image which a contrast process was made on, making a light irradiation process in the embossed (raising) X-ray image, storing and controlling its data and X-rays image provided by a series of image processing, printing X-rays pictorial image provided by a series of processes on the monitor or on the paper.

Furthermore, present invention provides a X-ray image processing system, comprising means for: capturing simple X-ray image in a computer, applying an embossing(raising) process on the X-ray image, applying a light irradiation process in the embossed (raising)X-ray image, storing and controlling its data and X-rays image provided by a series of image processing, printing X-rays pictorial image provided by a series of processes on the monitor or on the paper.

Furthermore, present invention provides a X-rays image processing system wherein the means for capturing said simple X-rays image into a computer is either one of the means for taking photograph X-rays pictorial image in a digital camera using film viewer, means for taking X-rays image in a computer with a scanner, sending X-rays pictorial image directly to a computer by machine unificated with CR (Computed Radiography).

Furthermore, present invention provides a x-rays pictorial image processing method to diagnose an orthopedics disease and an oral surgery disease, comprising a step of: capturing a photographed simple X-rays image in a computer, applying a contrast process on a X-rays image taken in a computer and/or a step of applying an embossing (raising) process to X-rays image, performing a light irradiating process in X-rays image made an embossment, storing and managing X-rays image provided by a series of image processing Furthermore, present invention provides a x-rays pictorial image processing method comprising: input means for inputting the inspection record of the subject, saving means for saving said inspection record as an inspection history every individual, means for said inspection record being collated with the inspection record that input in system at start, means for determining whether said inspection is reexamination or not, if it is reexamination, means for being selecting the last test result automatically, and being able to be displayed.

Furthermore, present invention provides an X-rays image processing program that is executable by a computer, comprising means for: capturing simple X-rays image diagnosing an orthopedics disease and an oral surgery disease with a computer in a computer, applying a contrast process on a X-rays image taken in a computer and/or applying an embossing (raising) process, performing a light irradiating process in X-rays image made an embossment, archiving facility extends, and for managing the X-rays image provided by a series of image processing, printing X-rays image provided by a series of processes on the monitor of the computer with representation and/or a printer.

Furthermore, present invention provides a distribution server device for distributing an X-ray image processing program performable in a computer and characterized to be functioned as means for: capturing a simple x-ray image for diagnosing an orthopedic disease and an oral surgery disease into the computer; applying a contrast process and/or an embossing (raising) process to an X-ray image captured into the computer; performing a light irradiation process in an embossed (raised) X-ray image; storing and controlling an X-ray image obtained from a series of the image processes; causing an X-ray image obtained from a series of the processes to be displayed in a monitor of the computer and/or printed by a printer; and distributing an X-ray image in accordance with a distribution request of a distribution destination.

Effect of the Invention

According to the present invention, orthopedic and oral surgery diseases being difficult or unable to read diagnostically in a conventional technique can be precisely judged under visual observation by applying a series of image processes, allowing planning of more appropriate treatment measures and elimination of redundant examinations, so that reduction of an economical burden for the patient and medical cost cutting can be achieved.

Since image processing time is a short period of time (about five minutes on average including entire processes), prompt clinical response is made possible. The processes simply applied to an existing simple x-ray image do not require radiation exposure exceeding thereof for the patient (reduction of a biological burden).

The image processing method according to the present can be realized by any one selected from a digital camera, transmitting unit type scanner, and CR image, in addition to a personal computer and software capable of processing an image, or software exclusively programmed to prevent an obstacle in executing the X-ray image processing system, so that easy introduction and space reduction without a space required for machine installation can be made possible (reduction of a physical burden).

Figure 1:
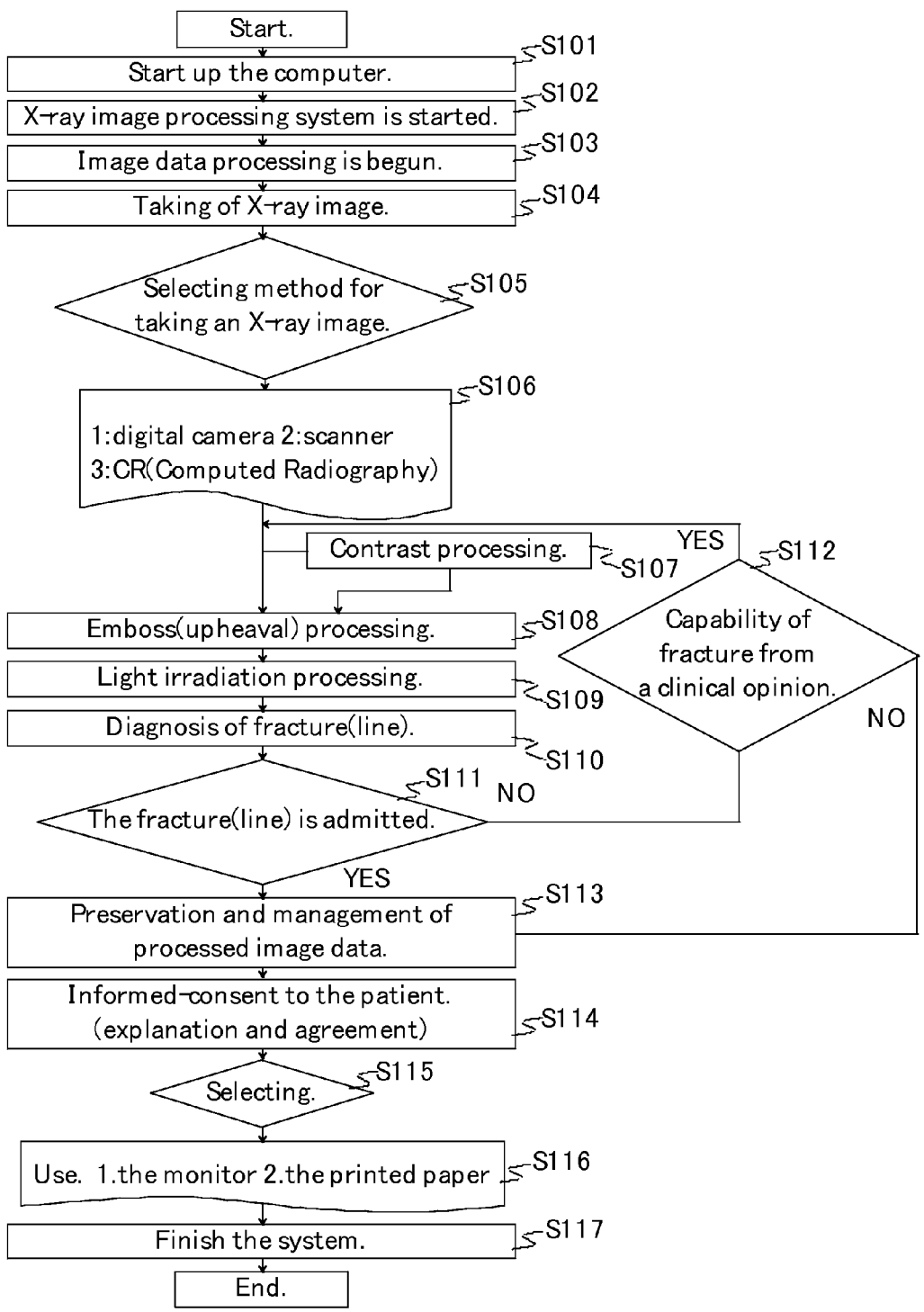
FIG. 1 is a flow diagram showing an operational flow in the case of using an X-ray image processing system.

20,21,22,23,25,26,30 Fracture(line)
32.35 40 Joint space narrowing
33. 36 Bony sclerosis/consolidation
34. Cyst formation
37. Formation of osteophytes
38. Condylar deformity
41. Crush
42. Focal necrosis

DESCRIPTION OF PREFERRED EMBODIMENTS

In the present system, a series of image processes are applied to an X-ray image for enhancing accuracy thereof in order to diagnose existence of diseases in orthopedics and oral surgery, thereby these diseases can be diagnosed in comparison with clinical findings. An image processing method applied here is as stated above. In an X-ray image obtained from a simple X-lay examination, an image is composed by the change (shade density) of the blackening degree. An example will be explained using a fracture being a representative orthopedic disease. The fracture is defined as a state in which continuity of bone tissue is completely or partially cut off. A bone is a three-dimensional structure substance, and if the continuity of bone tissue is cut off, a fracture area is considered to be dislocated even in a fine cut. However, a bone image obtained from a plane X-ray image provides a state to see the change (shade density) of the blackening degree, i.e. a shadow picture of a bone, and there are not a few cases in which a fine dislocation is difficult to confirm. Therefore, a process is added to bring a state in which trabeculae can be precisely confirmed by initially applying a contrast process to the change (shade density) of the blackening degree in accordance with necessity, and/or an embossing (raising) process is applied thereto, so that height is added to a plane X-ray image which is made two dimensional. A light irradiation process is further applied to add shade the two-dimensional X-ray image so that depth is added to height, thereby an image to be visually seen as if it is three-dimensionally floated can be obtained.

The word "embossing (raising) process" used in the present invention is meant not only to mold and raise or the like, but also to bring a plane image into a three-dimensional state. The embossing (raising) process implies to raise a plane image in accordance with light and shade supplied from the change of the blackening degree thereof, i.e. to arbitrarily provide a protruding amount by assuming that a blight area of the image (edge) is protruded relative to a dark area. A process and a step to bring a shadow image obtained from the simple X-ray examination into a three-dimensional state are called the embossing (raising) process in the present invention.

Moreover, the light irradiation process implies to irradiate light to an outline area raised as stated above from all angles so as to cause the area to be seemingly floated from the surface, i.e. to prepare shade which is made by the protruding amount with irradiated light in an arbitrary direction.

According to the present invention, the embossing (raising) process and the light irradiation process provide shade and a boundary line on a computer screen in an area with a suspected fracture (line) in the case of the fracture for example, so that dislocation and/or deformity of the fracture (line) or the like can be precisely diagnosed by existence of the shade and an output of the boundary line.

The embossing (raising) process and the light irradiation process are known image processing methods for preparing a three-dimensional image, in which the processes are executed in such a manner that a shadow area and direction are determined by setting values in a hypothetical height (10 pixels in a first embodiment) with a background as a reference, a hypothetical light irradiation angle (−90 degrees in the first embodiment), and an application capacity (270% in the first embodiment) with respect to an X-ray image captured in a computer. Moreover, the values described in the first embodiment are merely an example and not common in entire cases. Each of the values is required to be optimum and best to allow precise observation of shade and a boundary line in an area diagnosed as the fracture or the like when imaging diagnosis is made by applying the embossing (raising) process and the light irradiation process according to the present invention.

The light irradiation angle (shade direction) may be set by directly inputting an arbitrary angle of 0 to 360 degrees other than being set by default. It is also possible in the configuration to allow a setting of shade intensity.

To be more specific, the above processes are achieved by introducing an emboss filter (filter matrix) of 3×3 pixels using a total sum of respective elements as 0 for example. That is, due to digital processing, an X-ray image with each of the pixels gradually expressed in a dot matrix state is subjected to an arithmetic process for converting a gradation value in each of the pixels by using the emboss filter (emboss matrix). After executing the process by the emboss filter (filter matrix) in each of the pixels, 128 may be added to a converted gradation value in each of the pixels.

A direction to irradiate light can be modified by changing an arrangement of each of the elements in the emboss filter (emboss matrix). Moreover, the shade intensity is adjustable by setting, for example, 0.1 to 1 in a correction coefficient multiplied to a gradation value which was subjected to the process by the emboss filter (emboss matrix) so as to weaken shade in accordance with the decrease of the correction coefficient to be selected and intensify shade in accordance with the increase of the correction coefficient to be selected.

Each of the elements in the emboss filter (emboss matrix) can be variously set other than setting 0. ±1, and ±2, and the number of pixels can also be variously set to 5×5 pixels and 7×7 pixels or the like, in which a particularly preferable mode is to allow precise confirmation of a trabecular structure of a subject when the process was executed.

The first embodiment as an example of an image captured in a computer has pixel resolution of 24 dpi, data resolution of 400 dpi, and an information amount of 11.5 MB in order to execute the above process. An information capacity capable of executing the present system is dependent on a performance of a personal computer which executes the process. In the case of an image having a large information capacity, a process with a high accuracy is made possible, in which a personal computer exhibiting a high performance without a problem to execute the process is required. Moreover, in the case of a processed image attached and distributed by mail, it is necessary to decrease an information capacity with a less accuracy or compress the image, and an optimum selection is appropriately made in accordance with an object. The enumerated mail distribution method of a processed image is merely an example, and the distribution method is not limited thereto.

The contrast process applied before the embossing (raising) process and the light irradiation process is preferable to indicate the trabeculae distinctively. Although it is also possible to apply the contrast process after the embossing (raising) process and the light irradiation process, a maximum effect can be exhibited in the contrast process which is applied prior to the embossing (raising) process and the light irradiation process according to the present invention, thereby there is an advantage of improving an unclear image which is often seen in a simple X-ray photo obtained from conventional analog photographing, allowing the process to be executed in a satisfactory state.

The contrast process according to the present invention implies to correct an image so as to be preferable for executing the embossing (raising) process and the light irradiation process by adjusting a contrast between a dark colored part and a blight colored part. Particularly because an X-ray image has an extremely wide distribution of concentration from a dark part to a bright part, thereby it is effective in many cases in the present invention to execute the contrast process such as compressing a contrast of a bright part.

The contrast process is realized by selecting a desired value from predetermined setting values of −127 to +127, for example, using a slider and numeric value.

An amount (%) to increase or decrease the contrast should be determined by a relative relationship between the embossing (raising) process and the light irradiation process, and a particularly preferable mode is to allow confirmation of a trabecular structure most distinctively under visual observation.

Additionally, a known image correction method such as a brightness correction and a gamma correction may also be employed in accordance with necessity.

An application range in a series of the image processes is not exclusively adapted to orthopedic diseases. For example, it is applicable to breakage of teeth in a dental surgery. The orthopedic diseases include a representative fracture, osteoarthritis of the hip, avascular necrosis of the femoral head (ANF), and osteochondritis dissecans (OD) or the like. Other departments such as a department of internal medicine have a possibility to utilize the application range in a series of the image processes. The diseases are exemplarily stated to apply the X-ray image processing system and these diseases are merely an example, thereby an application range of the present invention is not limited thereto.

An initial step in a series of the image processes is to capture an X-ray image into the computer. It includes a method to photograph an X-ray image by a digital camera using a Schaukasten, a method to capture an X-ray image using the scanner, and a method to directly send an X-ray image to the computer by integration with a CR, in which a most applicable method is selected to capture an X-ray image depending on a situation. In the case of photographing an X-ray image by a digital camera on the Schaukasten, an X-ray image is desirably photographed by darkening a room or in a darkroom to prevent reflection, while careful attention is paid to reflection of a surrounding fluorescent light or the like. In the case of capturing an X-ray image by the scanner, the scanner with a function of an original transmitting unit is required. It is operationally most effective to directly send an X-ray image to the computer by integration with the CR, which requires large costs. A step to capture the X-ray image into the computer is an important step because it determines quality of subsequent processes thereafter.

Next, the contrast process is applied to the X-ray image captured in the computer. A contrast between brightness and darkness is initially applied to an X-ray image captured in the computer by various kinds of methods such as the digital camera and the scanner. More distinctive observation of trabeculae is therefore made possible, and the satisfactory contrast allows conversion into a state in which the change (shade density) of the blackening degree can be distinctly confirmed. Moreover, the contrast process is not necessarily required and it is determined appropriately whether or not to execute the contrast process. A case in which the contrast process is required is to have an unclear image such as a simple x-ray image obtained from analog photographing. In this case, the contrast process is added to obtain a satisfactory image and enhance results of subsequent processes thereafter. However, these cases are merely an example to apply the contrast process, and an application range of the contrast process is not limited thereto.

Figure 18:
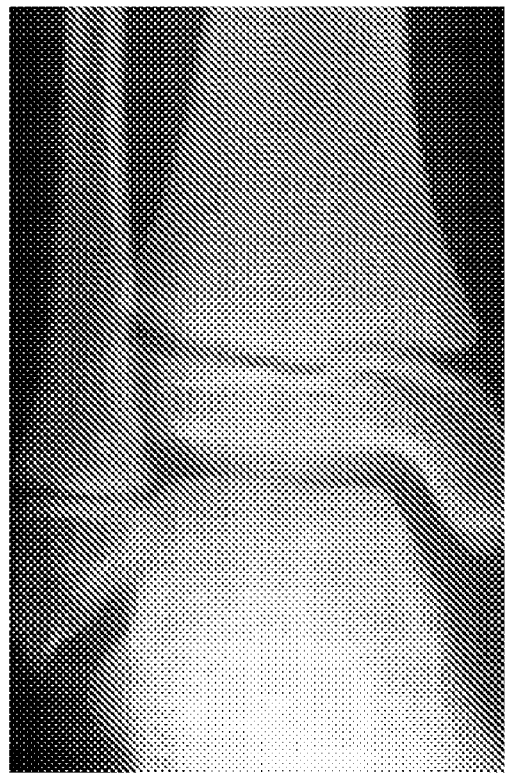
FIG. 18 is a diagram showing initial diagnosis of an unprocessed image in a case 1 of a first embodiment.
Figure 19:
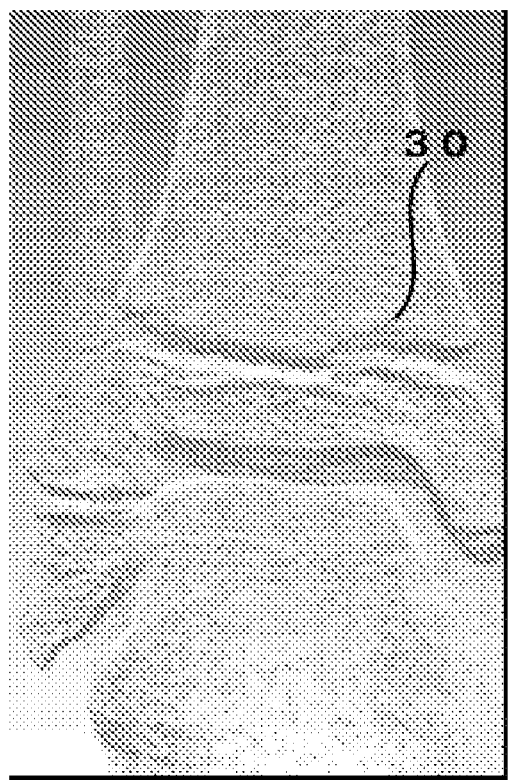
FIG. 19 is a diagram showing initial diagnosis of a processed image in a case 1 of a first embodiment.

Next, the embossing (raising) process is applied. Explanation will be made for the fracture as an example. The fracture is defined as a state in which the continuity of bone tissue is completely or partially cut off. However, the bone is actually a three-dimensional structure substance, and if the continuity of bone tissue is cut off in a fracture (line), a fracture area is considered to be dislocated even in a fine cut. That is, in the case of having a fine damage (fracture) in the trabeculae, there is an influence appearing to a fine change (shade density) of the blackening degree on the X-ray image, even though the fracture is not observed in general imaging findings, i.e. visual observation. The fine change (shade density) of the blackening degree is raised to allow determination of the fracture with the naked eye, enhancing accuracy of the imaging diagnosis. In place of the emboss process, a shallow relief process may be applied to obtain a similar effect (FIG. 18 and FIG. 19).

Next, the light irradiation process is executed for the X-ray image, irradiating light to an area with a suspected fracture from all angles. To be more specific, a light irradiation direction of software being used is changed to employ a light irradiation result from a direction in which the fracture line can be determined most significantly. The embossing (raising) process is applied to protrude the fine change (shade density) of the blackening degree in the fracture area for easy confirmation, and light is irradiated to the protrusion from all angles, adding shade to the fine raised change (shade density) of the blackening degree. Therefore, accuracy of the imaging diagnosis is further enhanced. Furthermore, existence of shade and an output of a boundary line in the fracture area allow confirmation of a dislocation direction in bone fragments, so that there is significant clinical meaning.

On the basis of the imaging findings obtained from an X-ray image with a series of the completed image processes and actual clinical findings, final diagnosis is made. As a reference of the imaging diagnosis, a fracture is diagnosed by unique shade to be seen in the X-ray image processing system and existence of a boundary line (fracture line) in an area with a fracture suspected from the clinical findings. Basic medical knowledge is required in this step.

Data obtained from a series of the image processes are stored in a control program of the computer. A recording medium which can be used for storing and controlling an X-ray image obtained from a series of the image processes includes, for example, a floppy (registered trademark), hard disc, optical hard disc, optical magnetic disc, CD-ROM, CD-R, magnetic tape, nonvolatile memory card, and ROM or the like. However, the enumerated recording media are merely an example, and a range of the recording medium is not limited thereto.

An X-ray image displayed in a monitor of the computer and/or printed out on the basis of an obtained X-ray image and the clinical findings is used for informed consent (explanation and agreement) for a patient.

FIRST EMBODIMENT

A first embodiment according to the present invention will be explained using FIG. 1 through FIG. 10.

The present embodiment relates to a step and effect in each of the processes of the X-ray image processing system. FIG. 1 shows an operational flow in the case of using a simple x-ray image processing system described in claim 1. As an initial operation, the computer is turned on (S101) to start the X-ray image processing system (S102), so as to start image processing (S103). In capturing the X-ray image (S104), a method to capture the X-ray image is selected (S105). The selection includes 1) digital camera, 2) scanner, and 3) computed radiography (CR) (S106). Of course, there is no limitation for the above selection of 1) digital camera, 2) scanner, and 3) CR as long as there is no problem recognized to realize the X-ray image processing system described in claim 1. As a process for an X-ray image captured into the computer by various kinds of methods, the contrast process is performed for the X-ray image captured in the computer (S107). However, this contrast process is not requisite. The embossing process can exclusively make contribution to improvement of the X-ray image without executing the contrast process.

A fracture will be explained as an example. The embossing (raising) process is performed for an X-ray image with application of the contrast process or an X-ray image without application of the contrast process (S108). The light irradiation process is performed for an X-ray image which was embossed or raised (S109). Diagnosis of a fracture (line) is made in an X-ray image obtained as a result. If the fracture (line) is not observed (S111), the processes are performed again for a suspected fracture (line) in consideration of the clinical findings (S112). In executing the processes again, used is a method to increase resolution and emphasize the contrast process or the like, and processed image data obtained through a series of the image processes are stored and controlled in the case of observing a fracture or the like and in the case of observing no fractures or the like (S113). When an X-ray image obtained from a series of the image processes is used for informed consent (agreement through explanation) for the patient (S114), an explanation method is selected (S115). The selection includes 1) monitor display, and 2) using a document printed out by a printer (S116). Of course, there is no limitation for the above selection of 1) monitor display, and 2) using a document printed out by a printer as long as there is no problem recognized to realize the X-ray image processing system described in claim 1. The X-ray image processing system is finished in a stage to complete the entire processes (S117).

Figure 2:
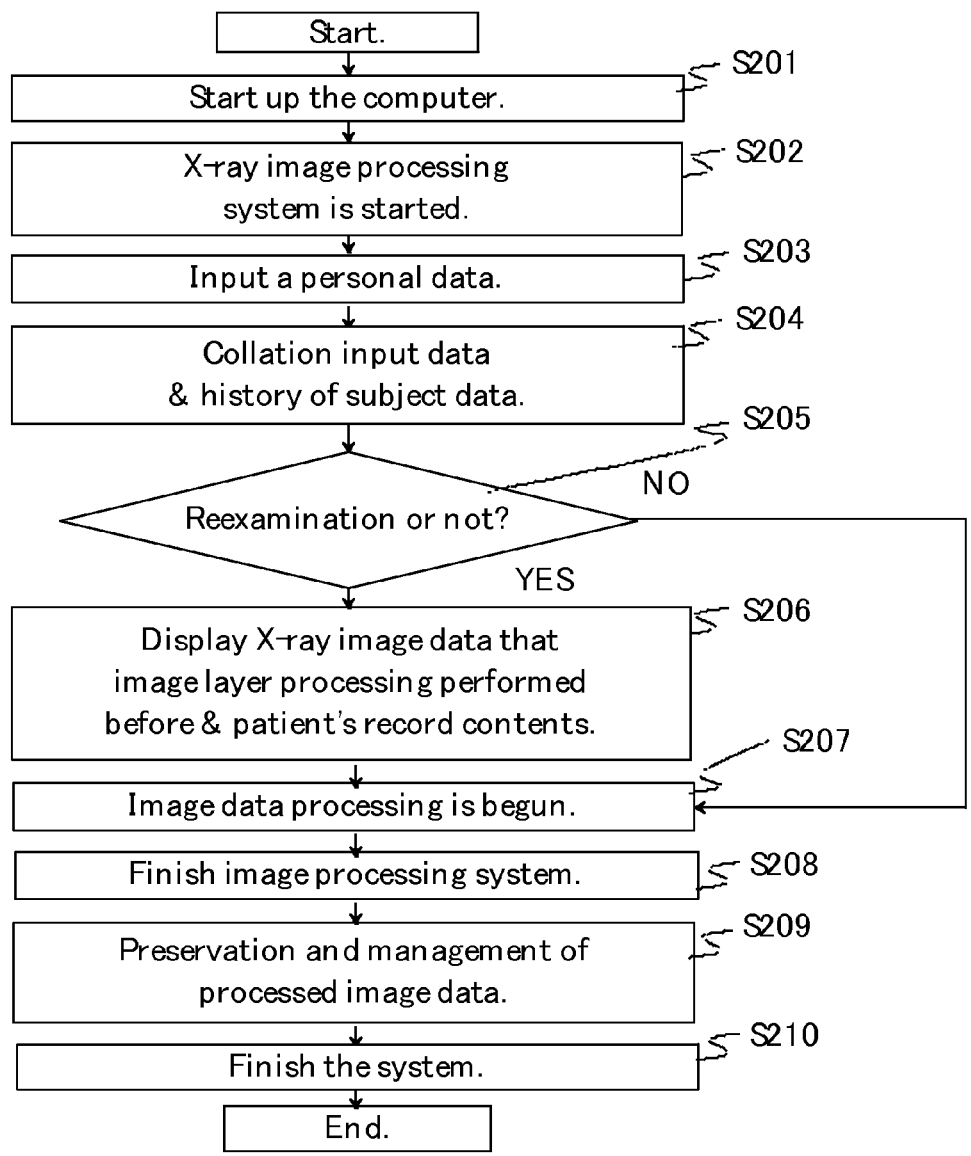
FIG. 2 is a flow diagram showing an operational flow in the case of reexamination using the X-ray image processing system.

This example relates to a process of each step and effect. FIG. 2 is showing a flow of process using reexamination in claim 5. First start a computer (S201), start up a image processing system(S202). Before executing the image processing, personal data of an examinee is inputted in a necessary item input column on a screen (S203). The input data is compared with an examined history of the examinee (S204). If the result indicates a reexamination (S205), X-ray image data of the previous image process and chart content are displayed (S206). In the case of the reexamination, X-ray image data of the previous image process and chart content are confirmed to start the image processing even if the reexamination is not indicated (S207). Stop the series of image processing (S208). Processed image data is saved (S209). Stop the image processing system(S210).

Search items to be used include a chart number, name, phone number, and health insurance category. The items enumerated are merely an example, and a range of the search items is not limited thereto.

Figure 3:
FIG. 3 is a whole diagram in which an X-ray image is captured by a digital camera in a first embodiment.
Figure 4A:
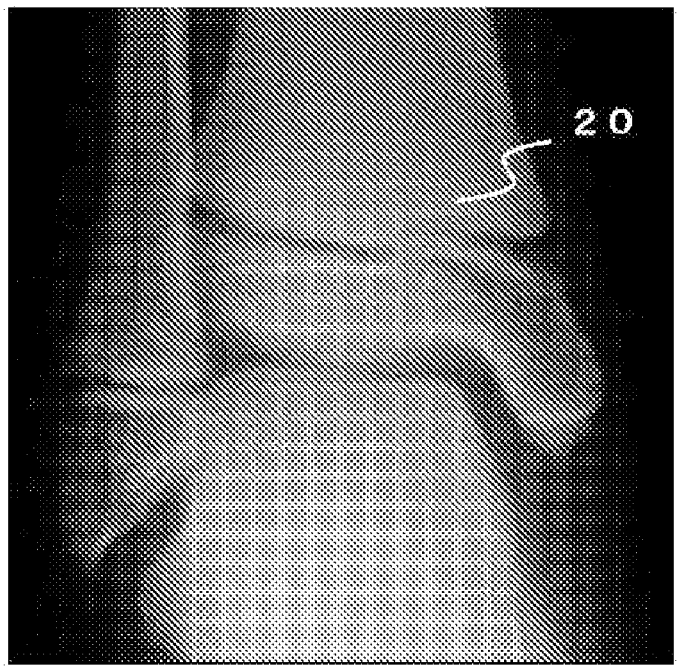
FIG. 4A is a diagram in which an X-ray image is captured by a digital camera in a first embodiment.
Figure 4B:
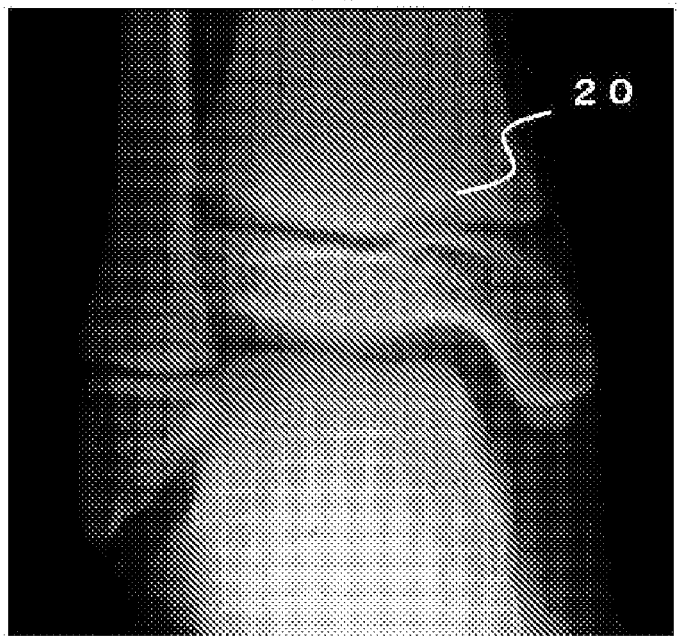
FIG. 4B is a diagram in which an X-ray image is captured by the scanner in a first embodiment.

FIG. 3 is a whole diagram in which an X-ray image is captured by a digital camera in a first embodiment.) FIG. 4A is a diagram in which an X-ray image is captured by a digital camera in a first embodiment. FIG. 4B is a diagram in which an X-ray image is captured by the scanner in a first embodiment. It is difficult to diagnose a fracture (line) from the imaging findings in a state of both FIG. 4A and FIG. 4B. It is on the basis of the fact that initial diagnosis and a second opinion fail to reach diagnosis of a Salter-Harris fracture type II.

Figure 5A:
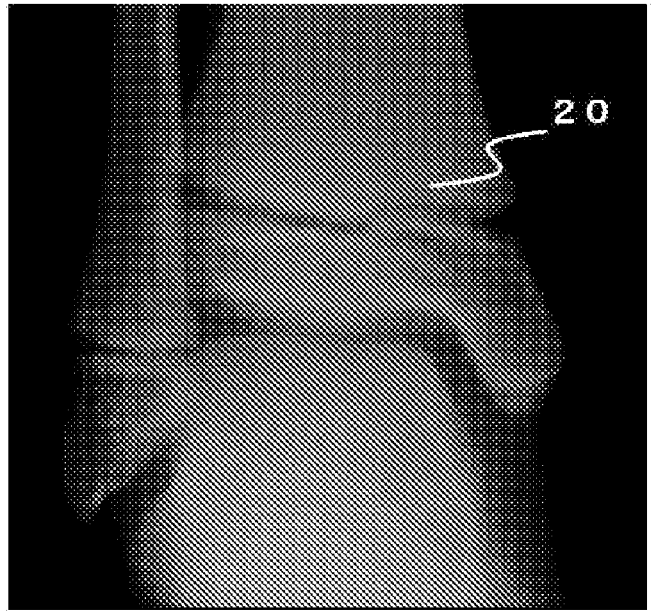
FIG. 5A is a diagram in which a contrast process is applied to the image captured by the digital camera in the first embodiment.
Figure 5B:
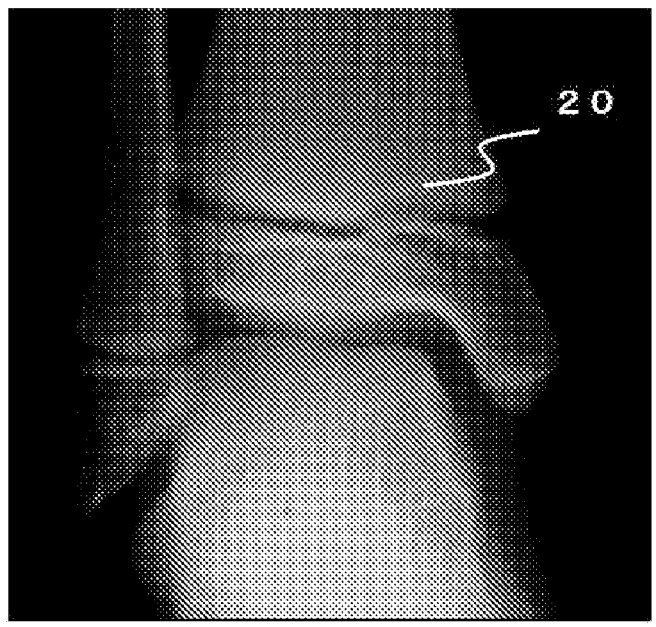
FIG. 5B is a diagram in which a contrast process is applied to the image captured by the scanner in a first embodiment.

FIG. 5A is a diagram in which a contrast process is applied to the image captured by the digital camera in the first embodiment. FIG. 5B is a diagram in which a contrast process is applied to the image captured by the scanner in a first embodiment.

The contrast process allows confirmation of a seemingly fracture (line) image (20) in an area of localized tenderness claimed by the patient in the clinical findings.

Figure 6A:
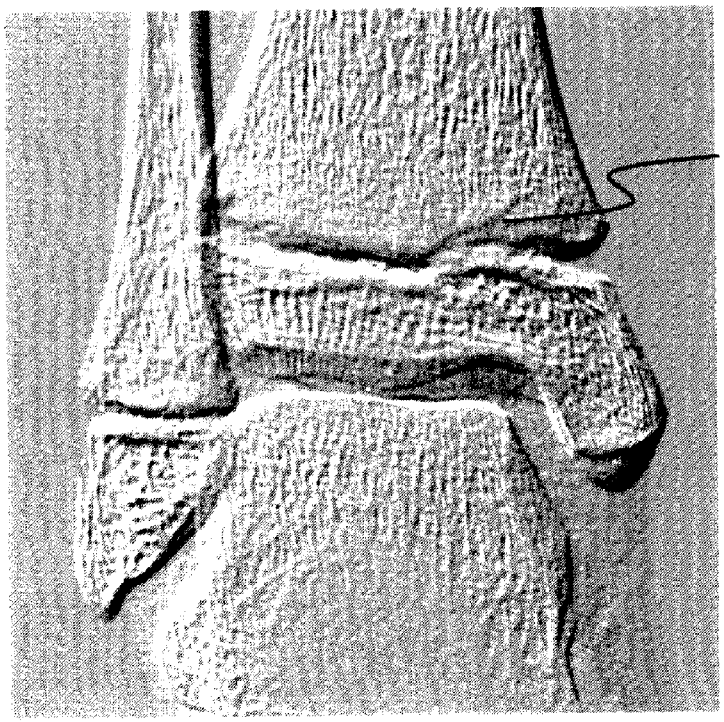
FIG. 6A is a diagram in which a embossing (raising) process is applied to the image captured by the digital camera in the first embodiment.
Figure 6B:
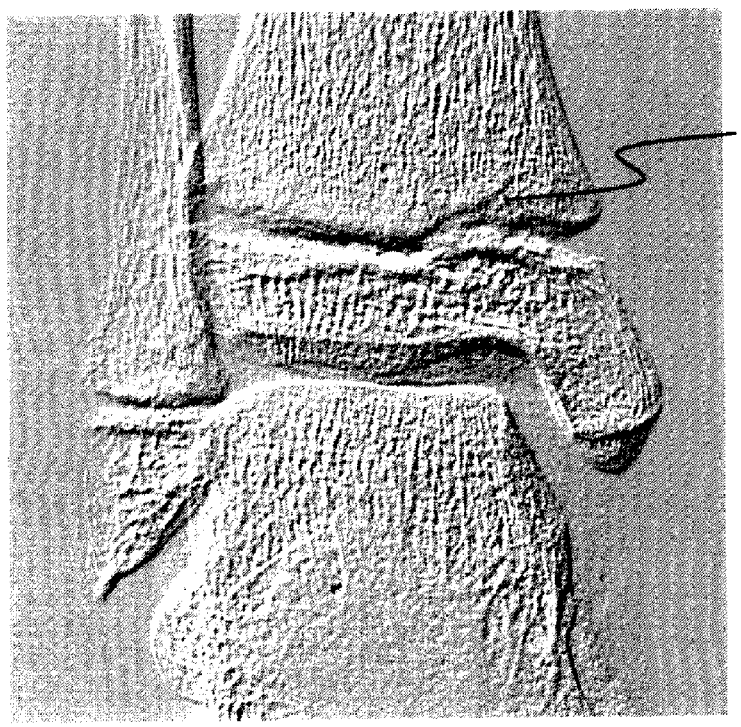
FIG. 6B is a diagram in which an embossing (raising) process is applied to the image captured by the scanner in the first embodiment.
Figure 7A:
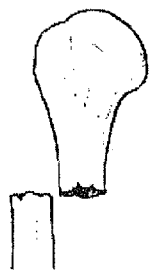
FIG. 7 is a diagram showing a classification of dislocation structures by shapes.
Figure 7B:
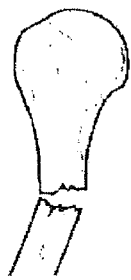
Figure 7C:
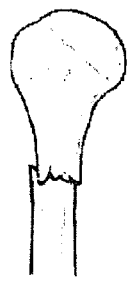
Figure 7D:
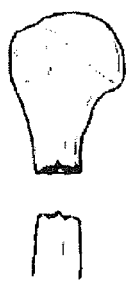
Figure 7E:

FIG. 6A is a diagram in which a embossing (raising) process is applied to the image captured by the digital camera in the first embodiment. FIG. 6B is a diagram in which a embossing (raising) process is applied to the image captured by the scanner in the first embodiment. Due to the application of the embossing (raising) process and the light irradiation process, a fracture (line) image (21) can be distinctively confirmed in an area of localized tenderness claimed by the patient in the clinical findings.

FIG. 7 is a diagram showing a classification of dislocation structures by shapes. A fracture causes a gap and bending in edges of a fracture from each other. A positional change of a bone is called dislocation, and this dislocation exhibits deformity by appearances. A fracture is defined as a state in which continuity of bone tissue is completely or partially cut off. That is, the continuity of bone tissue is cut off, so that the fracture area is considered to be dislocated even in a fine cut. Attention was paid to this dislocation in the X-ray image processing system, and fine dislocation which is difficult to confirm with the naked eye is made three-dimensional or raised, further irradiating light to prepare shade, so that the fracture (line) area is floated for confirmation.

Figure 8:
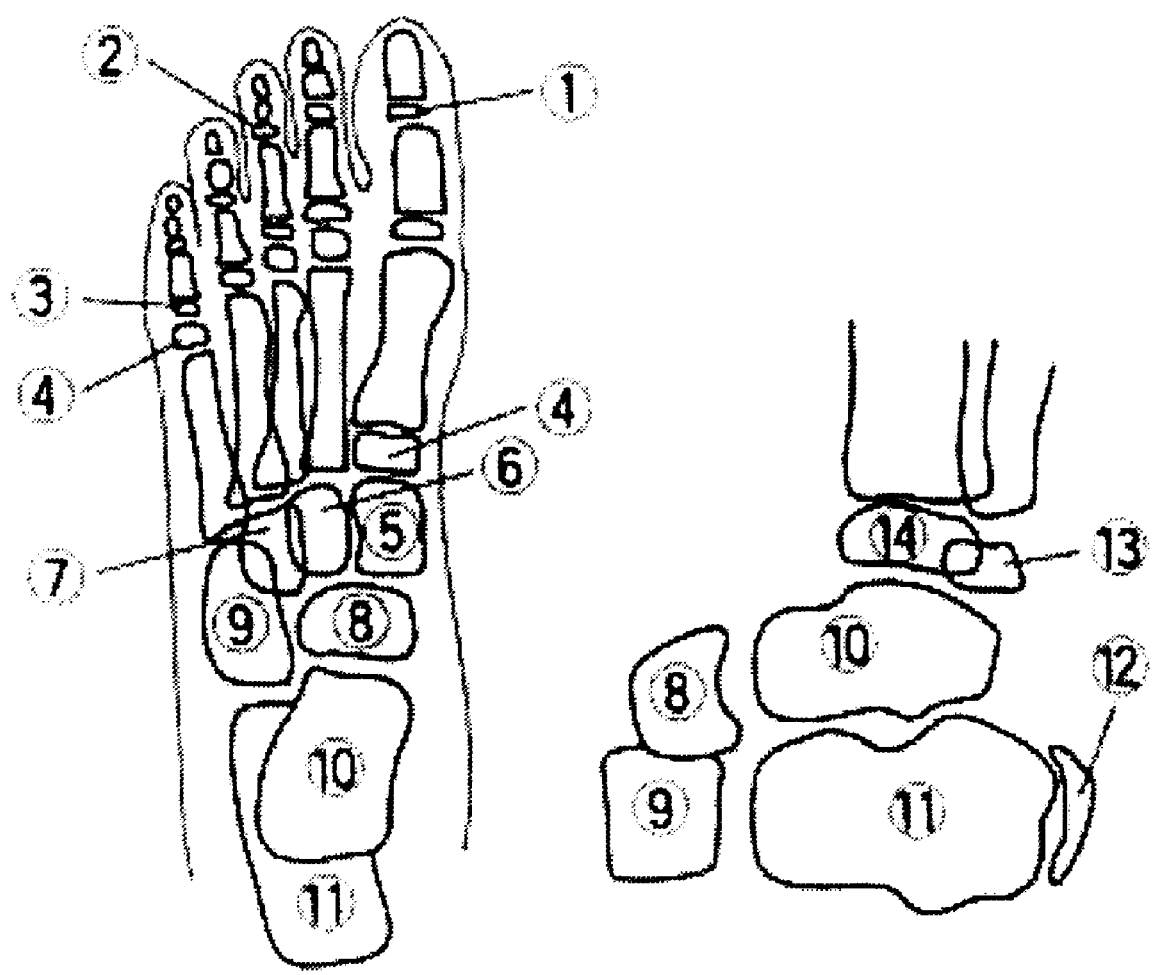
FIG. 8 is a diagram showing generation and closure of an epiphyseal nucleus.

FIG. 8 is a diagram showing generation and closure of an epiphyseal nucleus Cartilage accounts for a majority of epiphyseal, in which an ossification center in the epiphysis appears in accordance with a development of enchondral ossification due to growth and increases gradually, and eventually fuses with the metaphysic. A patient in the first embodiment has injured a distal epiphyseal nucleus in the tibia 14 in a right ankle joint in the diagram.

Figure 9:
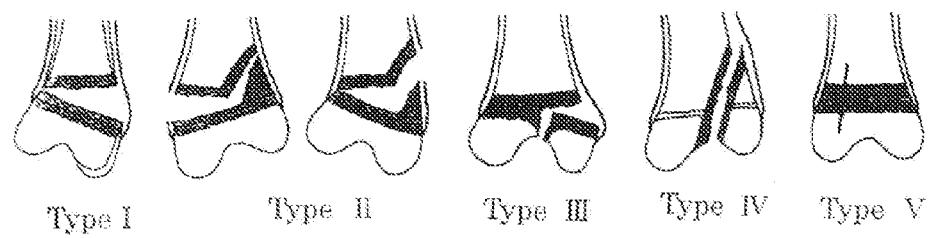
FIG. 9 is a diagram showing a classification (Salter-Harris fracture classification) of an injury of the epiphyseal plate.

FIG. 9 is a diagram showing a classification (Salter-Harris fracture classification) of an injury of the epiphyseal plate. Roman letters are used in the FIG. 9 instead of Arabic figures in the text, and either one of two letters matches each part.

Type 1: This is a complete separation of the epiphyseal plate without fractures of the epiphyseal and diaphyseal areas. Newborns, infants, and young children are more likely to develop and recover it without growth failure.

Type 2: This is the most common type that the epiphyseal plate is accompanied with the os trigonum fragments of the diaphyseal area. Older children are more likely to develop it. Easy reset is expected to present with less growth failure.

Type 3: Unlike type 2, the separation of the epiphyseal plate is accompanied with the epiphysis fragments, suggesting a rare injury in which fracture lines reach within the joints. Appropriate reset in the articular surface yields favorable results, leading to a rare onset of growth failure.

Type 4: This is a fracture longitudinally running from the articular surface beyond the epiphyseal plate to the diaphyseal end. It is often identified in lateral malleolus fracture of the humerus with high possibility of growth failure. Open reset and fixation are required to appropriately treat the articular surface and the epiphyseal line. Incomplete reset may result in poor prognosis.

Type 5: This is a crush injury of the epiphyseal plate with a longitudinal external force, which is often observed in the regions of the knee joint and ankle joint. No dislocation makes the diagnosis difficult. The crushed epiphyseal plate occurs early closure, growth failure and deformities, suggesting the poorest prognosis.

Figure 10A:
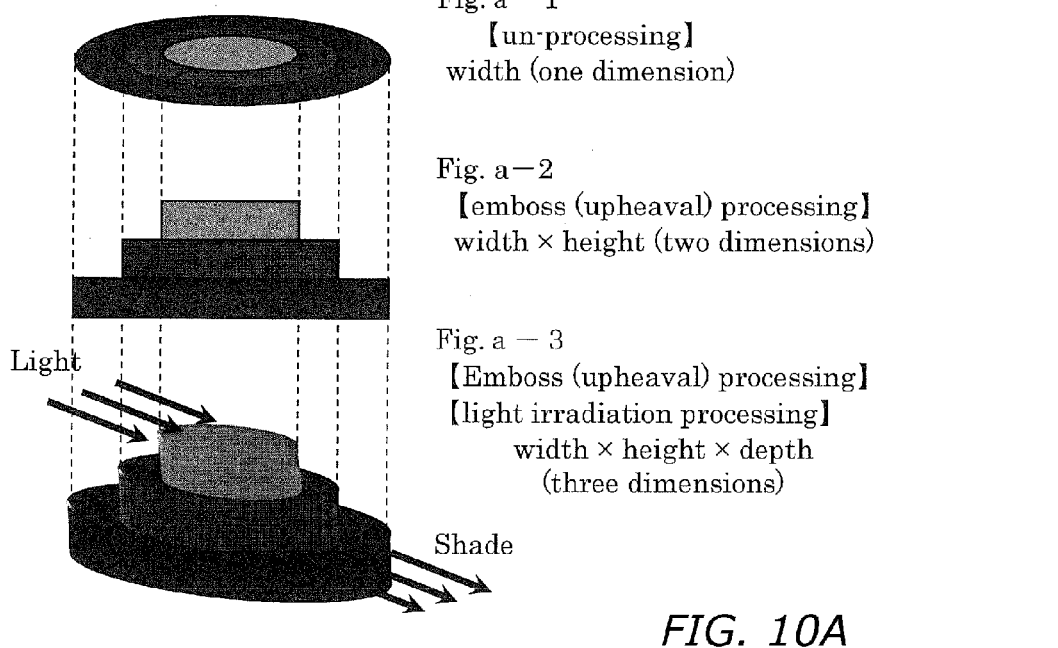
FIG. 10A is an explanatory diagram showing a theory of embossing (raising) and light irradiation processes.
Figure 10B:
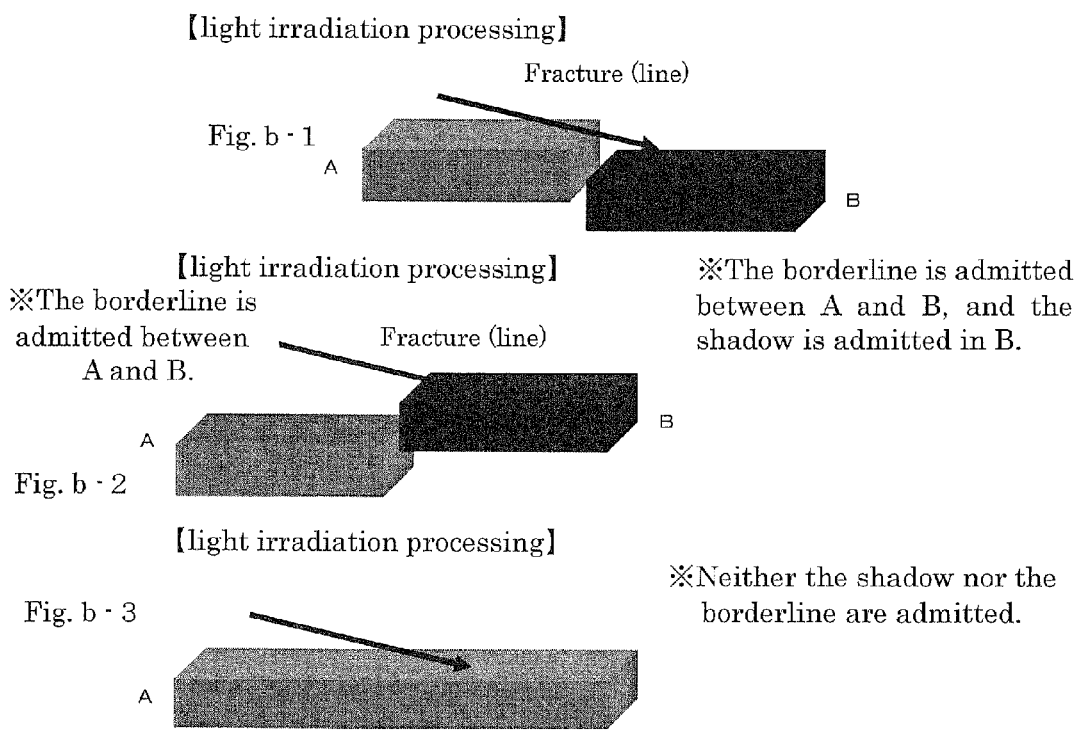
FIG. 10B is an explanatory diagram showing a theory of light irradiation processes.

FIG. 10A is an explanatory diagram showing a theory of embossing (raising) and light irradiation processes. FIG. 10B is an explanatory diagram showing a theory of light irradiation processes.

In an explanatory diagram of FIG. 10A showing a theory of the embossing (raising) process and the light irradiation process, FIG. a-1 typically shows an X-ray image. Color concentration indicates a change (shade density) of a blackening degree to compose the X-ray image. FIG. a-2 typically shows the embossing (raising) process applied to an unprocessed X-ray image. This exhibits conversion from a one-dimensional state to a two-dimensional state by embossing (raising) FIG. a-1 which simply had width so as to add height. In FIG. a-3, the light irradiation process is further applied to FIG. a-2 so as to add shade, thereby depth is added to width and height. Therefore, FIG. a-3 is made three-dimensional. An explanatory diagram of FIG. 10B showing a theory of the light irradiation process typically exhibits a diagnosis method of the fracture (line) and a determination reference of dislocation. In a case in FIG. b-1, i.e. the fracture (line) initially exists between A and B and if further upward dislocation of A relative to B are admitted, a boundary line is observed between A and B by the light irradiation process from the left direction, and shade of A appears to B. Therefore, existence of a fracture (line) between A and B and a positional relationship of A and B can be understood. Moreover, if the fracture (line) exists between A and B, and further downward dislocation of A relative to B is admitted, the boundary line is observed between A and B by the light irradiation process from the left direction without appearance of shade of A to B as shown in FIG. b-2. Therefore, existence of the fracture (line) between A and B and a positional relationship of A and B can be understood. If A does not have the fracture (line) as shown in FIG. b-3, the light irradiation process from the left direction does not exhibit the boundary line and shade. Therefore, A can be diagnosed as having no fracture (line).

A Clinical Document in Embodiment 1

Patient: 11 years old boy

Cause for disease: Aug. 29, 2003, around 5 pm. The patient was injured the lower part of the right lower leg (tibia) in a fall from play equipments (tire) during play at a park. Further details were not recorded the chart because the patient did not remember.

Injury day: Aug. 29, 2003

Beginning of the treatment: Aug. 29, 2003 The treatment period is 18 days.

Wound name: opinion of home doctor is a right foot joint blow.

Since the fracture was suspected from clinical findings, the patient visited another doctor to seek a second opinion (Sep. 1, 2003). The diagnosis of separation of the epiphyseal line in the right ankle joint (suspicion of the Salter-Harris fracture type) was considered by the doctor. Even though a fracture of the inferior-medial part of the right lower leg (tibia) was suspected from the clinical manifestations, clear imaging findings failed to be obtained.

Findings: tenderness (+), swelling (+), indirect pain (+), fever (37.5° C.) were observed in medial margins of the right tibia. After the injury, the patient was unable to walk with the heel of the affected extremity due to severe pain, causing a leaping gait with the healthy extremity.

Simple X-ray findings: A diagnosis of bruise on the ankle joint was made at nearby hospital without imaging findings (Aug. 29, 2003). The patient visited another doctor to seek a second opinion, and the diagnosis of slight separation of the epiphyseal line (suspicion of the Salter-Harris fracture type I) was made by the doctor (Sep. 1, 2003). Even though a fracture of the inferior-medial part of the right lower leg (tibia) was suspected from clinical manifestations, clear imaging findings failed to be obtained.

Course: Aug. 29, 2003 (hereinafter, 2003 is omitted). The patient was injured the lower part of the right lower leg (tibia) in a fall from play equipments (tire) during play at a park. Since a pain was not observed in both of the medial malleolus and lateral malleolus of the right ankle joint, the injury appeared not to be ankle sprain. A tibial fracture was suspected from tenderness in the medial margins of the tibia. Even though body temperature (37.5° C., fever) and slightly indirect pain were observed in the patients, a diagnosis of bruise on the ankle joint was made at a nearby hospital.

August 30: Circumference of the medial malleolus and lateral malleolus R<affected side>22.4 cm/L<healthy side>21.5 cm August 30: Site of the injury: R: 18.5 cm L: 18.5 cm August 30: Indirect pain (+). Body temperature was 37.1° C.

September 1st: Warmth in the right lower leg was reduced. The body temperature returned to normal temperature. The patient visited another doctor to seek a second opinion because of further suspicion of tibial fracture. The diagnosis of separation of the epiphyseal line (the Salter-Harris fracture type 1) was considered by the doctor.

September 3: Tenderness of the diaphyseal end was reduced, leading to permission of walking with Splinting.

September 5: According to the patient reports, there was no problem in walking with Splinting.

September 10: Splinting was removed based on excellent prognosis, followed by permission of walking alone (leap, running, and Japanese sitting style were prohibited).

September 11: After removal of the Splinting, increased physical activity induced warmth, resulting in refixation with Splinting.

September 13: While a pain in the ankle joint was resolved, jumping behavior caused another pain.

September 16: Splinting was removed due to reduction of the pain in the ankle joint.

September 17: The doctor gave an instruction that number of icing should be increased because tenderness was still observed in the diaphyseal end of the lower part of the right lower leg (tibia).

September 18: Since there was a slight difference of 1 cm between circumferences of the medial malleolus and lateral malleolus in the affected and healthy extremities without indirect pain and pain in walking of the right lower leg, walking alone was permitted at this time.

September 26: While indirect pain and percussion tenderness in the area of separation of the epiphyseal line were not detected, tenderness was still observed in medial margins of the right tibia.

September 29: The patient reported that he participated in a relay at athletic meeting yesterday and felt a slight pain on the affected area during the relay, suggesting that the pain has remained even one month after the injury. Lastly, regarding the use of a part of the patient's chart, permission to use and publish was obtained from the patient based on the Private Information Protection Law.

According to the Salter-Harris fracture type I in the case 1 of the first embodiment, the case 1 in the first embodiment has exclusively separation of epiphyseal area as an injured area without a fracture line observed in general. However, this case includes a fracture in the inferior-medial part of the right lower leg (tibia), thereby considered to be the Salter-Harris fracture type II. If the present system was initially applied, it is considered that a fracture area could have been distinctively observed as shown in FIG. 6, allowing diagnosis of the Salter-Harris fracture type II. Although a patient in the first embodiment was initially diagnosed as the Salter-Harris fracture type I including a bruise on the ankle joint and separation of the epiphyseal line, the patient is diagnosed as the Salter-Harris fracture type II by the X-ray image processing system. Inconsistency between the imaging findings and the clinical findings is revealed here. As stated above, inconsistency between the imaging findings and the clinical findings can be improved by the present invention.

An epiphyseal growthplate is an important cartilage tissue to control a growth of a longitudinal axis of a bone. An area to be injured in an epihyseal growthplate is a hypertrophied cell layer and a calcified cartilage layer with the dynamically weakest characteristics in many cases. The injury causes various degrees of a growth failure and deformity depending on a degree thereof. The Salter-Harris fracture classification is most widely used and easy to use. Attention should be paid in treatment for the fact that an injury of an epiphyseal growthplate, which controls growth of a bone of an infant occasionally, causes a remarkable growth failure and progressive deformity depending on the type and quality of treatment, and careful diagnosis with accurate reset and follow-up is required. If generation of deformity starts due to early partial closure of an epiphyseal growthplate, it is necessary to cut off a bone crosslink of a closed area for grafting fat and cartilage (Langenskield operation) as early as possible. If deformity is unfortunately accomplished, it is impossible to avoid generation of osteoarthritis in due course without adjusting alignment of an adjacent joint by corrective osteotomy.

EXAMPLE 2

A second embodiment according to the present invention will be explained using FIG. 11 through FIG. 15.

A fracture of the carpal scaphoid is a serious fracture generated when a strong push is applied to a palmar, which is overlooked and simply treated as a sprain and bruise in many cases. It is because discovery of a fracture line is difficult with a dual directional X-ray photo obtained immediately after the injury. If a patient has a pain continued for a long period of time due to a sprain and bruise, it is necessary to confirm existence of a serious fracture by photographing an X-ray oblique image again. There is a case that blood circulation to the carpal scaphoid is supplied from a distal part and a central part, and not supplied from a proximal part. Therefore, considered is a possibility of delay in recovery of the fracture and necrosis of proximal bone fragments. In a treatment, it takes six to twelve weeks for bone union. If there is a delay in bone union and suspected aseptic necrosis of proximal bone fragments, bone grafting is performed.

A Clinical Document in Embodiment 2

Patient: 39 years old man

Cause for disease: May 23, 2004. A patient has injured a left hand pushed by falling down to a left side in skateboarding.

Injury day: May 23, 2004

Beginning of treatment: May 24, 2004. The period of treatment is 38 days.

Wound name: A fracture of carpal bone in the left hand (fracture of the carpal scaphoid)

Opinion: A patient visits a hospital claiming a pain of the left wrist on the following day of the injury. Swelling and warmth in the periphery of the left hand joint are observed with a body temperature of 37° C. (normal temperature of 36.5° C.), observing tenderness (++) in a snuffbox. On the day of the injury, the patient was capable of moving the left hand joint, carrying baggage with pain and having alcohol intake. Today (diagnosis date of May 24, 2004), the patient is diagnosed as a fracture of carpal bone in the left hand (fracture of the carpal scaphoid) at orthopedics in a nearby hospital.

Course: May 24, 2004 (after 2004 is omitted): The patient visits a hospital claiming a pain of the left wrist on the following day of the injury. Swelling and warmth in the periphery of the left hand joint are observed with a body temperature of 37° C. (normal temperature of 36.5° C.), observing tenderness (++) in the snuffbox. On the day of the injury, the patient was capable of moving a left hand joint, carrying baggage with pain and having alcohol intake.

Today (diagnosis date of May 24, 2004): the patient is diagnosed as the fracture of carpal bone in the left hand (fracture of the carpal scaphoid) at orthopedics in a nearby hospital.

May 25: Spontaneous pain (++) on the ulnar side of the left forearm

May 26: The patient was capable of sleeping with a subsided spontaneous pain today.

May 28: Decompression is performed with cotton, followed by applying dorsal splinting with a hydraulic cast material.

May 29: An internal pressure is reduced without a problem of wearing an outfit.

May 31: The patient claims lassitude from third time of a finger erecting exercise.

June 4: Swelling of the finger remains.

June 7: An X-ray examination performed at orthopedics in the nearby hospital exhibits callus, so that the patient is diagnosed to have no worries of pseudoarthrosis/non union.

June 9: In accordance with finger exercise for a long period of time, tenosynovitis-like symptoms occurs in abductor muscle of the thumb, but the symptom is removed by icing.

June 12: Localized tenderness in a fractured area remains.

June 19: A slight degree of swelling is observed in the finger.

June 23: The patient falls down backwardly. At that time, a push is made for the left hand without appearance of a pain.

June 24: The symptom in the fracture area is almost removed with a weakened grip observed.

R (healthy side) (1) 38.0 kg (2) 36.5 kg

L (affected side) (1) 24.0 kg (2) 16.5 kg

June 30: Improvement of the grip is observed.

R (healthy side) (1) 37.5 kg (2) 41.0 kg

L (affected side) (1) 29.5 kg (2) 30.0 kg

July 10: Clinical course of the symptom is good.

July 16: Although the symptom is satisfactory, the grip is not completely recovered.

August 9: Substantial recovery of the grip is observed, and a clinical course of the symptom is good, reaching completion of recovery as of today.

R (healthy side) (1) 43.0 kg (2) 41.0 kg

L (affected side) (1) 37.0 kg (2) 38.0 kg

The case 2 in the second embodiment exhibits a typical fracture of the carpal scaphoid in a carpal bone. This case has a better course than a general fracture of the carpal scaphoid, without complication of sequelae. In the imaging diagnosis, diagnosis of the fracture is obtained by the simple X-ray examination. In this case, the clinical findings and the imaging findings are consistent with each other, having a satisfactory selection of treatment measures.

Figure 11:
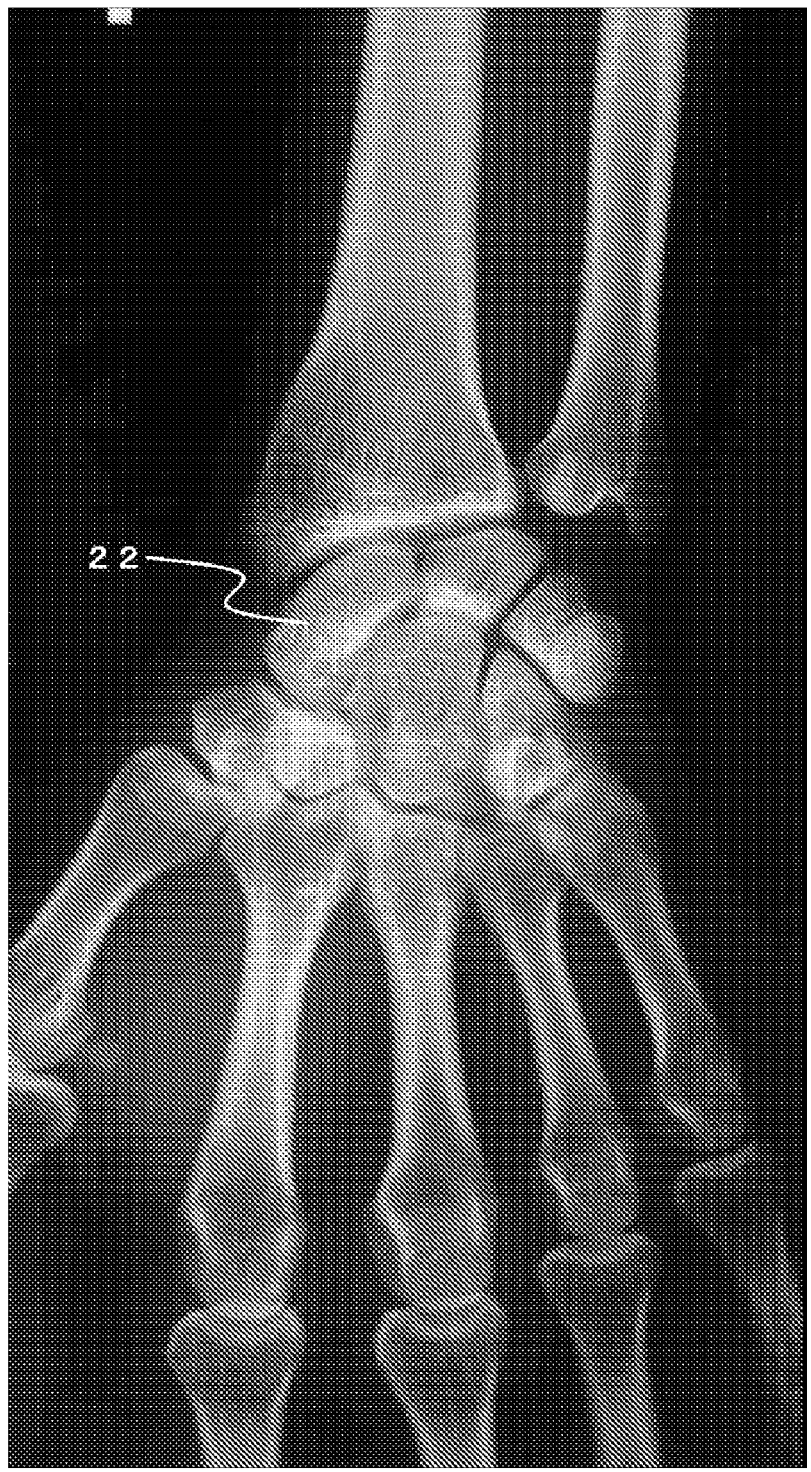
FIG. 11 is a whole diagram in which an X-ray image is captured by a digital camera in a second embodiment.
Figure 12A:
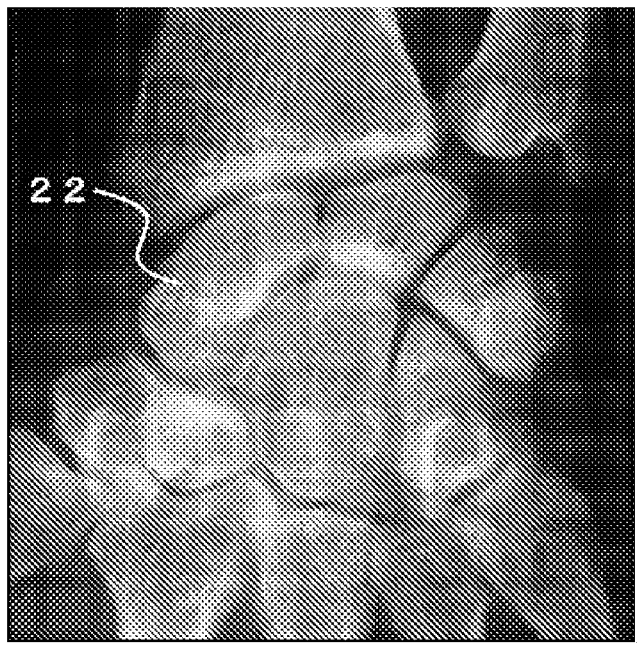
FIG. 12A is a diagram in which an X-ray image is captured by a digital camera in a second embodiment.
Figure 12B:
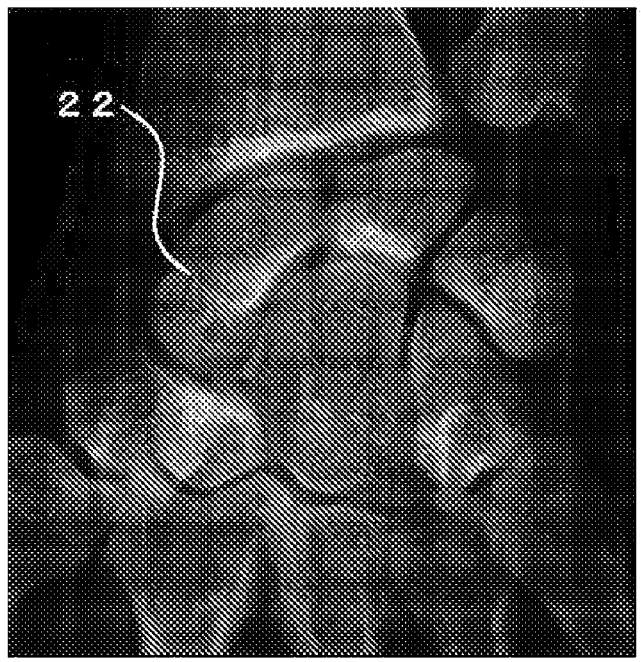
FIG. 12B is a whole diagram in which an X-ray image is captured by a scanner in a second embodiment.
Figure 13A:
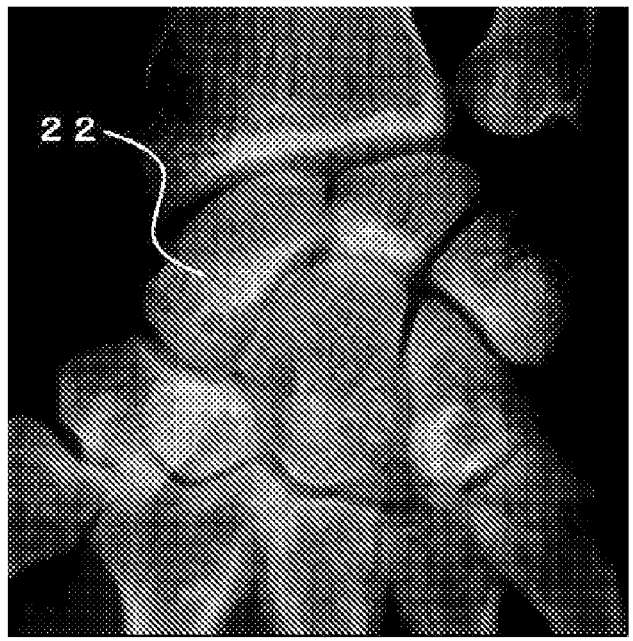
FIG. 13A is a diagram in which a contrast process is applied to an X-ray image captured by a digital camera in a second embodiment.
Figure 13B:
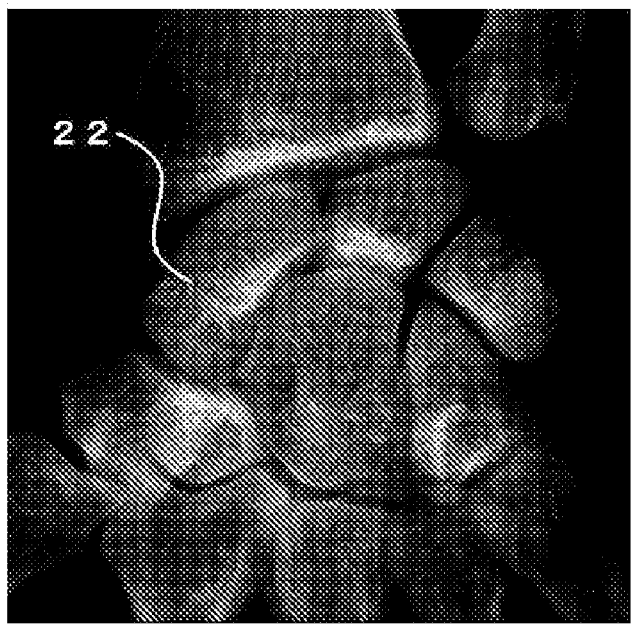
FIG. 13B is a diagram in which a contrast process is applied to an X-ray image captured by a scanner in a second embodiment.

FIG. 11 is an entire view of an X-ray image which was captured by a digital camera in the second embodiment. FIG. 12A is a diagram in which an X-ray image was captured by the digital camera in the second embodiment. FIG. 12B is a diagram in which an X-ray image was captured by the scanner in the second embodiment. A fracture (line) 22 is already observed in the one third distal part of the navicular nodule in the imaging findings before application of the processes. FIG. 13A is a diagram in which the contrast process was applied to an image captured by the digital camera in the second embodiment, and FIG. 13B is a diagram in which the contrast process was applied to an image captured by the scanner. Application of the contrast process allows confirmation of the fracture (line) 22 more distinctively.

Figure 14A:
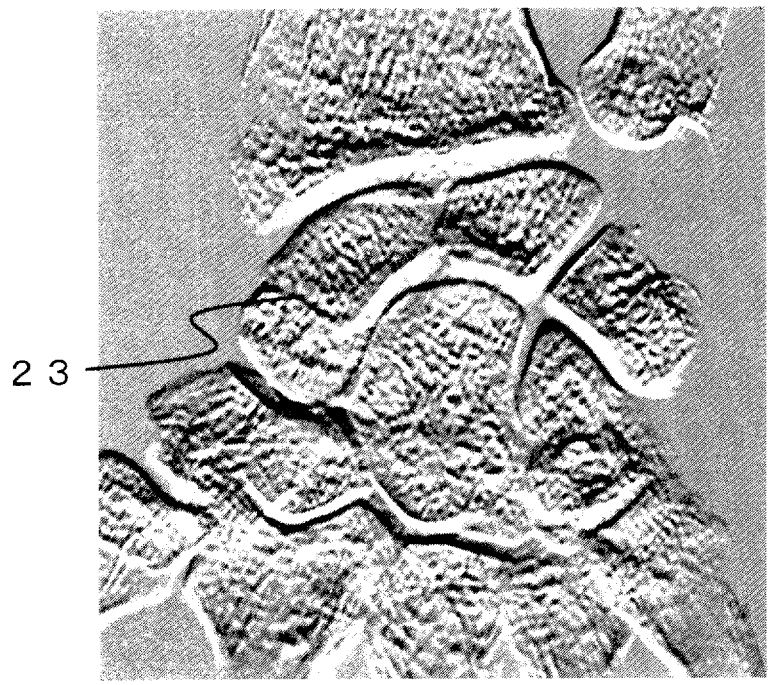
FIG. 14A is a diagram in which a embossing (raising) and light irradiation process is applied to the image captured by the digital camera in the second embodiment.
Figure 14B:
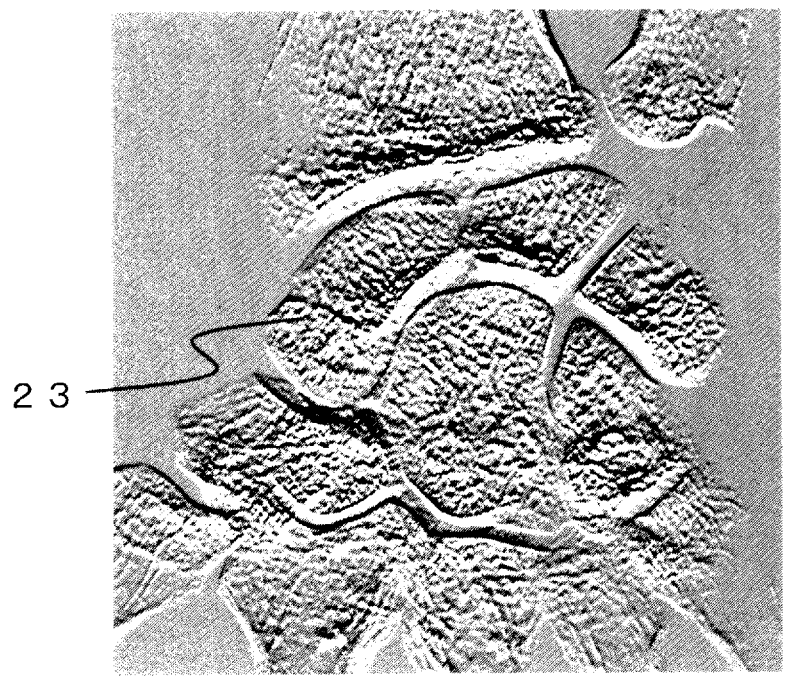
FIG. 14B is a diagram in which a embossing (raising) and light irradiation process is applied to the image captured by the scanner in the second embodiment.
Figure 15:
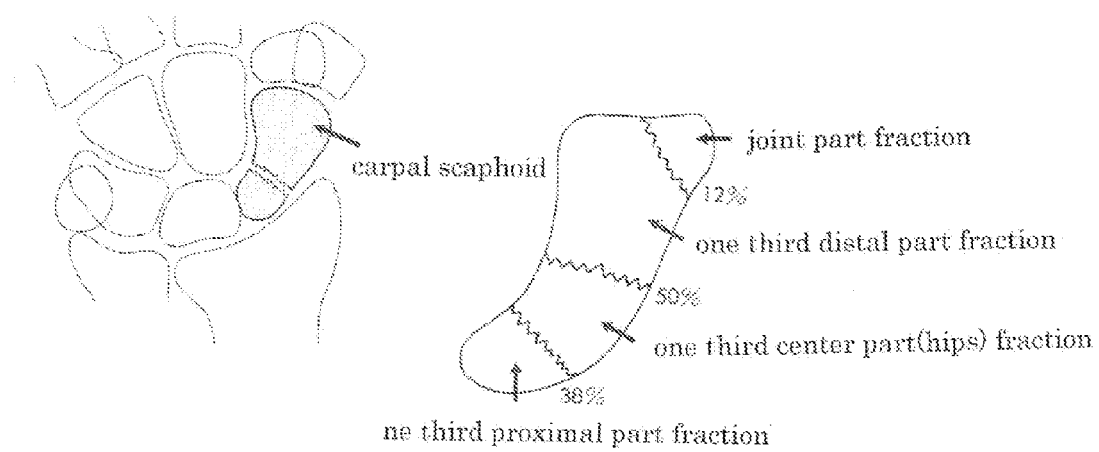
FIG. 15 is a diagram showing a classification of a fracture on the navicular.

FIG. 14A is a diagram in which the embossing (raising) process and the light irradiation process were applied to an image captured by the digital camera in the second embodiment, and FIG. 14B is a diagram in which the embossing (raising) process and the light irradiation process were applied to an image captured by the scanner in the second embodiment. Application of the embossing (raising) process and the light irradiation process allows confirmation of a fracture (line) 23 more distinctively. FIG. 15 is a diagram showing a classification of fractures in the carpal scaphoid. In the second embodiment, a fracture is observed in the one third distal part.

Attention should be paid for complete consistency in diagnosis of a fracture of the carpal scaphoid among the imaging findings from an image with application of the image processing according to the present system, the clinical findings, and the imaging findings from an unprocessed X-ray image. This confirms accuracy of the imaging diagnosis in the fracture (line) according to the present system, exhibiting an effect thereof in diagnosis of the fracture.

EXAMPLE 3

Figure 16A:
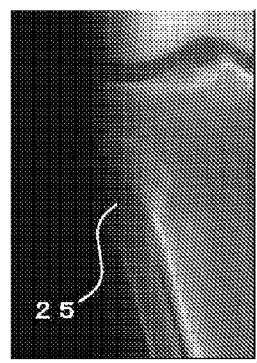
FIG. 16A is a diagram showing initial diagnosis of an unprocessed image in a case 3 of a third embodiment.
Figure 16B:
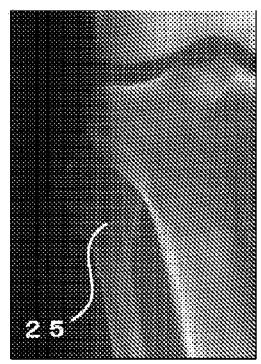
FIG. 16B is a diagram showing 2 weeks later diagnosis of an unprocessed image in a case 3 of a third embodiment.
Figure 16C:
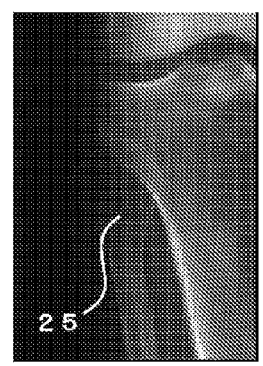
FIG. 16C is a diagram showing three weeks later diagram of the unprocessed image in the case 3 of the third embodiment.
Figure 17A:
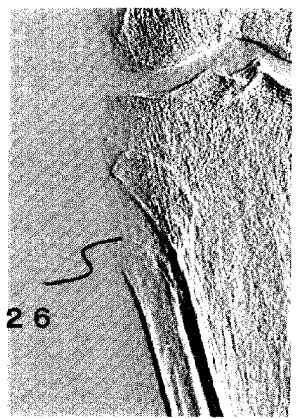
FIG. 17A is a diagram showing initial diagnosis of a processed image in a case 3 of a third embodiment.
Figure 17B:
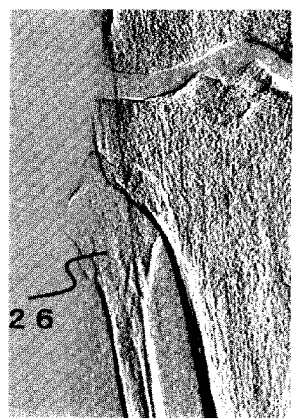
FIG. 17B is a diagram showing 2 weeks later diagnosis of a processed image in a case 3 of a third embodiment.
Figure 17C:
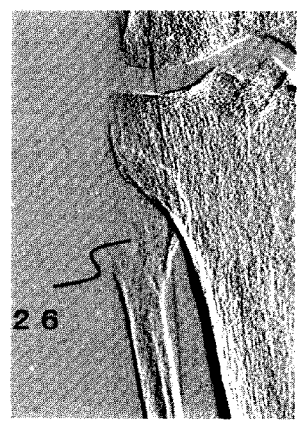
FIG. 17C is a diagram showing three weeks later diagram of a processed image in the case 3 of the third embodiment.

A third embodiment according to the present invention will be explained using FIG. 16 through FIG. 17.

Case 3:

Patient: 49 years old man

Mechanism: a patient has injured a head of the right fibula by falling off from stairs.

Injury day: Jan. 24, 2005

Beginning of treatment: Jan. 24, 2005. The period of treatment is 27 days.

Wound name: A fracture of head of the right fibula

Opinion: The patient visits a hospital claiming a pain in a head of the right fibula on the following day of the injury. There is observed swelling, a difference in circumference against a healthy side, a pain at the time of walking, and a spontaneous pain without observation of ecchymoses, in which a fracture is suspected from the clinical findings due to significant tenderness and a beating pain in the said area, so that a detailed examination is requested for orthopedics in a nearby hospital (Jan. 25, 2005). The patient is diagnosed as a fracture of head of the right fibula in the same hospital.

From the simple x-ray imaging findings, a fracture is observed in the head of the right fibula.

This exhibits a case in which the fracture is suspected from the clinical findings to reach fracture diagnosis. The patient was intoxicated with alcohol at the time of being injured and does not remember the order of the injury, and it is considered that the patient presumably had a bruise at the time of falling off from the stairs. The fracture was suspected from the clinical findings, and detailed examination was requested for orthopedics in a nearby hospital, thereby the fracture was revealed. A fracture 25 was observed in the head of the fibula without adding the image process according to the present system (FIGS. 16A to 16C), and fixation was applied due to no dislocation observed, resulting in satisfactory prognosis. From images subjected to the image process according to the present system (FIGS. 17A to 17C), it was also possible to obtain the imaging findings to observe a fracture 26 in the same area with an unprocessed image.

EXAMPLE 4

Figure 20A:
FIG. 20A is a diagram showing an unprocessed R(healthy extremity) image in a case 4 of a forth embodiment.
Figure 20B:
FIG. 20B is a diagram showing an unprocessed L(affected extremity) image in a case 4 of a forth embodiment.
Figure 21A:
FIG. 21A is a diagram showing a processed R(healthy extremity) image in a case 4 of a forth embodiment.
Figure 21B:
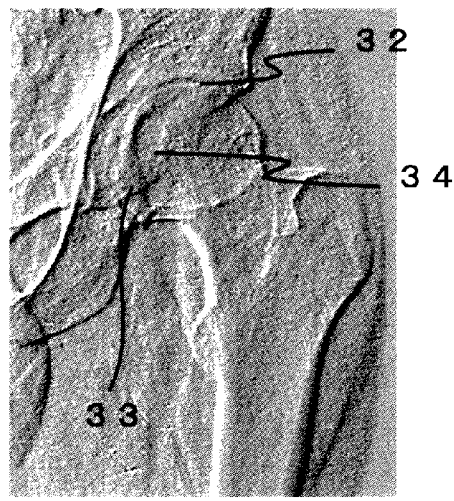
FIG. 21B is a diagram showing a processed L(affected extremity ) image in a case 4 of a forth embodiment.

A forth embodiment according to the present invention will be explained using FIG. 20 through FIG. 21.

Case 4: This case exhibits an initial state of osteoarthritis of the hip (R: healthy side, L: affected side). As shown in FIGS. 20a, 20b, 21a and 21b, the process is added to observe joint space narrowing 32, a bony sclerosis/consolidation 33, and cyst formation 34 more distinctively.

Osteoarthritis of the hip can be classified into a primary coxarthrosis of the hip with unclear original diseases, and a secondary coxarthrosis occurring in succession after a certain disease. A patient claims coxodynia, restriction in movements, and difficulty in walking. Coxodynia is worsened by walking and movements, and lessened by a rest. However, a patient claims a pain at rest and a pain at night in progressive coxodynia. Diagnosis can be easily made by the clinical findings and the imaging findings while paying attention to questioning for a history of acetabular dysplasia and congenital dislocation of the hip or acetabular dysplasia. In the simple X-ray examination, findings such as an ill-fitting joint, joint space narrowing, bony sclerosis/consolidation, cyst formation, and formation of osteophytes are observed and classified into four categories of acetabular dysplasia, primary coxarthrosis, advanced-stage coxarthrosis, and end-stage coxarthrosis by the simple X-ray examination. In order to obtain further detailed information, examinations such as an X-ray CT and MRI are required in general.

EXAMPLE 5

Figure 22:
FIG. 22 is a diagram showing an unprocessed image in a case 5 of a fifth embodiment: diagram showing a standing position front face L.
Figure 23:
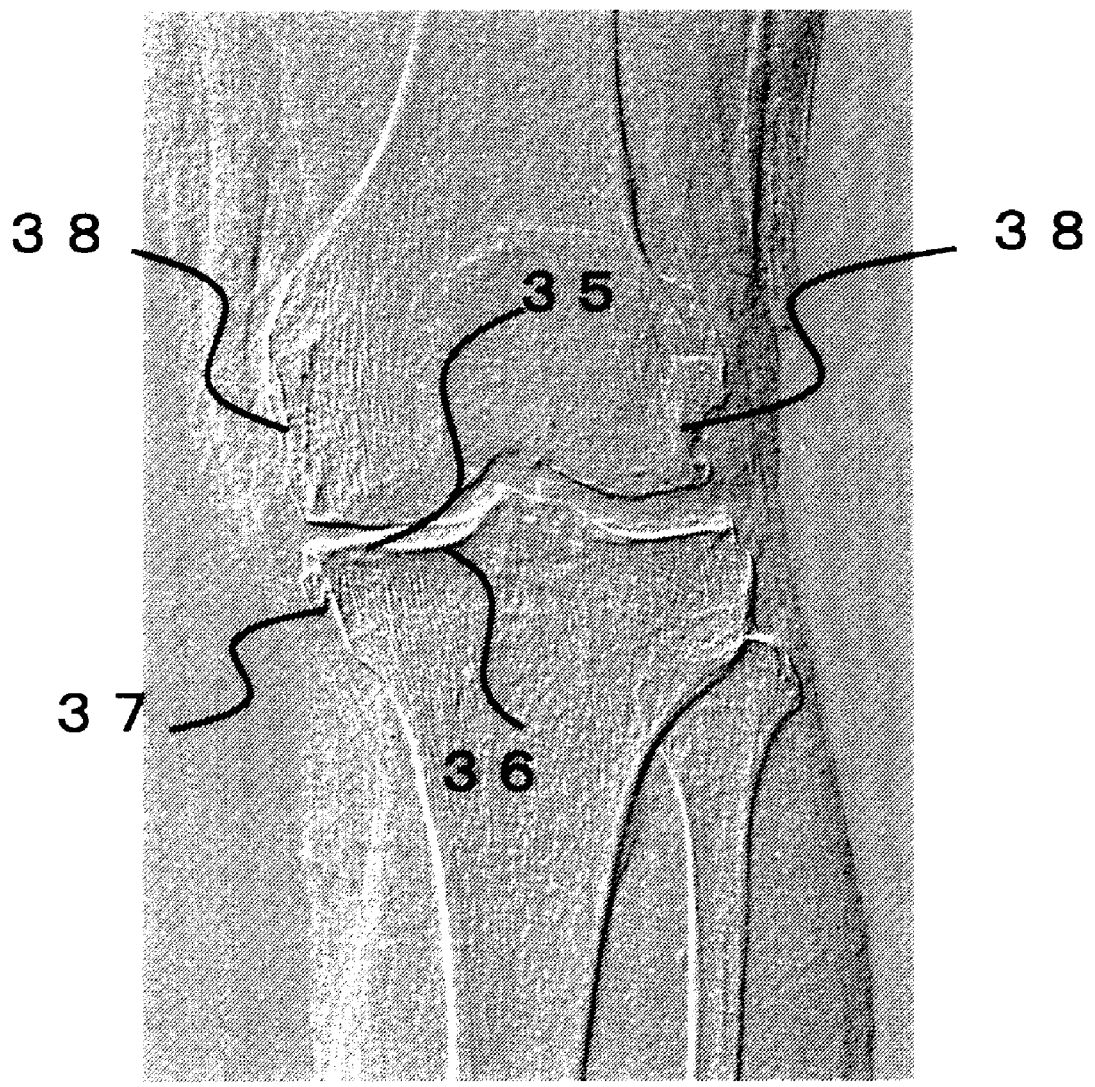
FIG. 23 is a diagram showing a processed image in a case 5 of a fifth embodiment: diagram showing a standing position front face L.
Figure 24A:
FIG. 24A is a diagram showing an unprocessed image in a case 6 of a sixth embodiment: diagram showing a front R(healthy extremity).
Figure 24B:
FIG. 24B is a diagram showing an unprocessed L(affected extremity) front image in a case 6 of a sixth embodiment.
Figure 25A:
FIG. 25A is a diagram showing a processed R(healthy extremity) front image in a case 6 of a sixth embodiment.
Figure 25B:
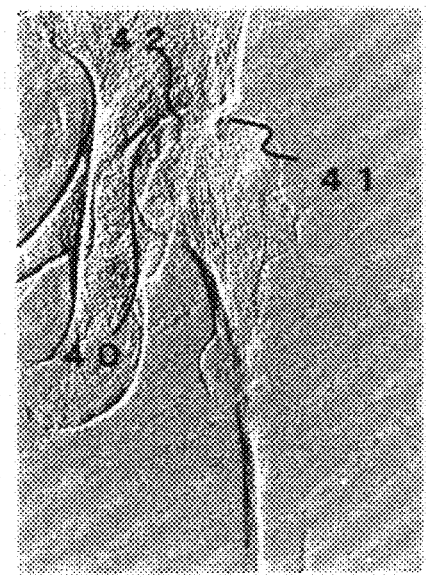
FIG. 25B is a diagram showing a processed L(affected extremity) front image in a case 6 of a sixth embodiment.
Figure 26A:
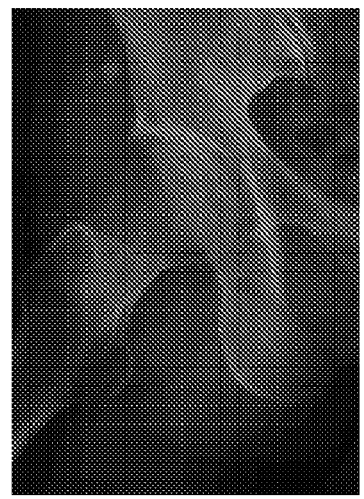
FIG. 26A is a diagram showing an unprocessed R(healthy extremity) Lauenstein image in a case 6 of a sixth embodiment.
Figure 26B:
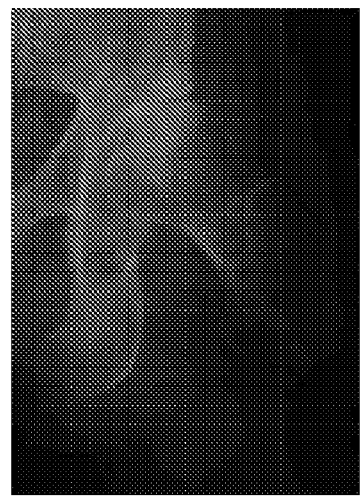
FIG. 26B is a diagram showing an unprocessed L(affected extremity) Lauenstein image in a case 6 of a sixth embodiment.
Figure 27A:
FIG. 27A is a diagram showing a processed R(healthy extremity) Lauenstein image in a case 6 of a sixth embodiment.
Figure 27B:
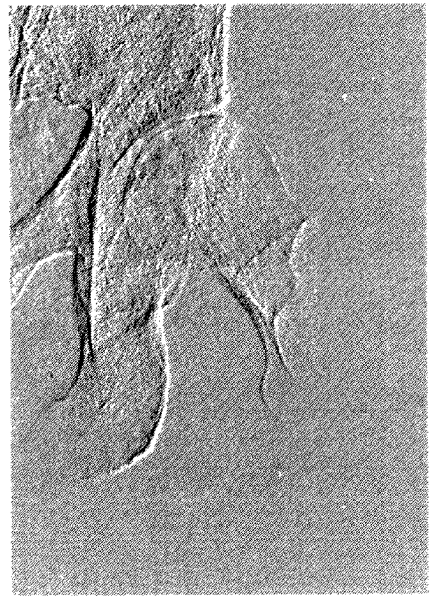
FIG. 27B is a diagram showing a processed L(affected extremity) Lauenstein image in a case 6 of a sixth embodiment.
Figure 28:
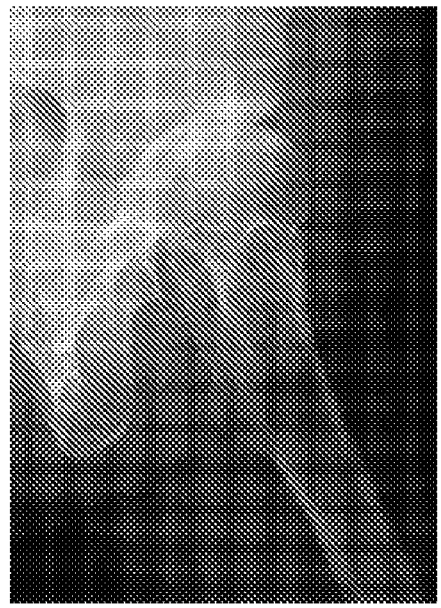
FIG. 28 is a diagram showing an unprocessed L(affected extremity) axial image in a case 6 of a sixth embodiment.
Figure 29:
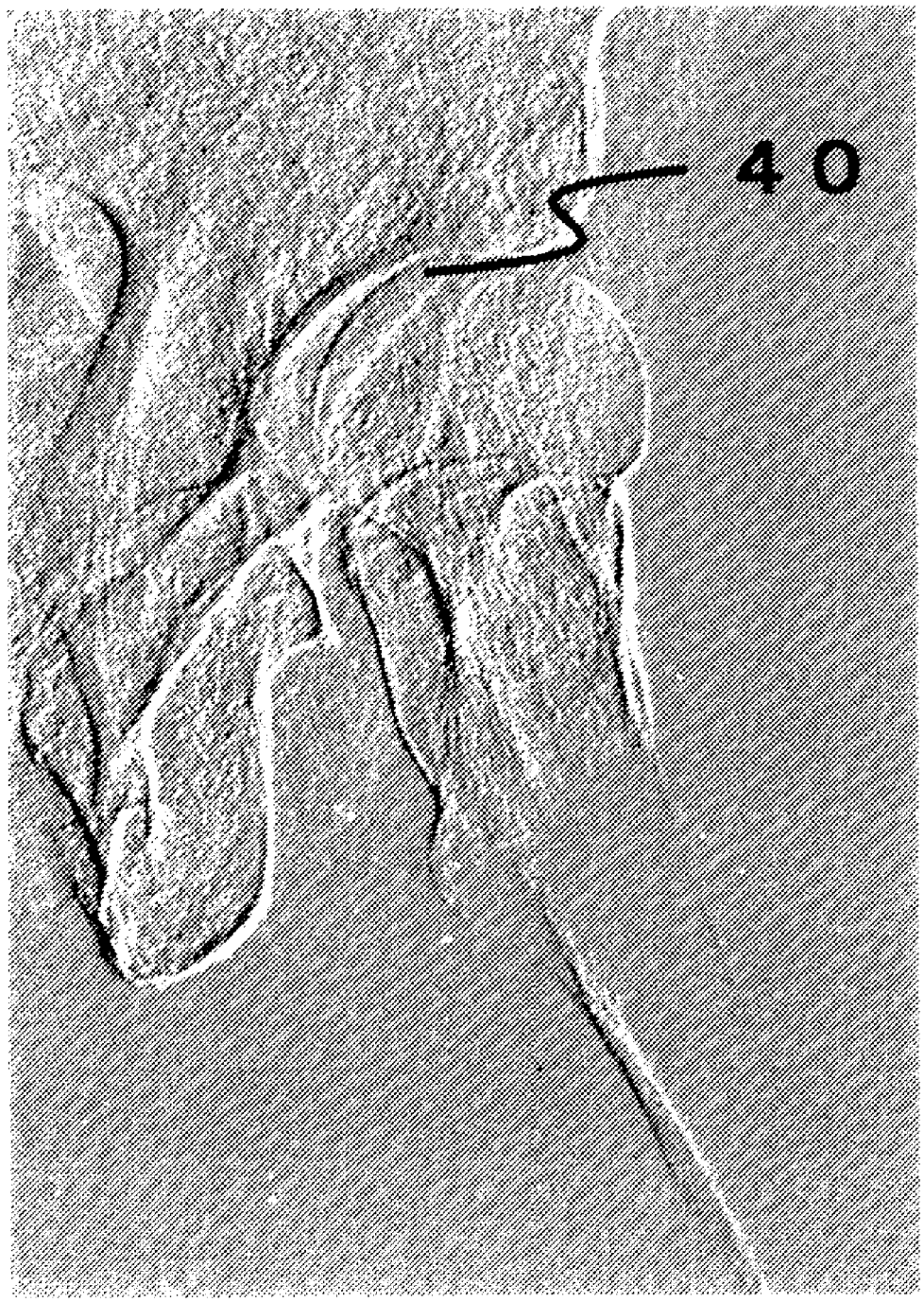
FIG. 29 is a diagram showing a processed L(affected extremity) axial image in a case 6 of the sixth embodiment.

A fifth embodiment according to the present invention will be explained using FIG. 22 through FIG. 23.

Case 5: This case exhibits osteoarthritis of the knee (standing L: affected side). As shown in FIGS. 22 and 23, the process is added to more distinctively observe joint space narrowing 35, a bony sclerosis/consolidation 36, formation of osteophytes 37, and condylar deformation 38 or the like in the medial condyle.

Osteoarthritis of the knee is a progressive degenerative disease of a cartilage and bone generated by aging and friction of the joint cartilage. The causes are divided into primary and secondary causes, in which precise causes such as a metabolic disease and congenital disorder are included in the secondary cause. Generation of osteoarthritis is observed more in weight-bearing joints such as a knee joint, hip joint, ankle joint, and spine with weight burden than non-weight-bearing joints such as a shoulder joint, elbow joint, and wrist joint without weight burden. Diagnosis is determined by the simple X-ray examination in general. In the imaging findings by the simple X-ray examination, there is observed joint space narrowing, formation of osteophytes, sclerosis/consolidation, condylar deformation, joint surface deficiency, cyst formation, and varus knee (a bow-leg state) or the like.

EXAMPLE 6

A sixth embodiment according to the present invention will be explained using FIG. 24 through FIG. 29.

Case 6: This case exhibits an initial state of avascular necrosis of the femoral head (ANF) (R: health side, L: affected side). As shown in FIGS. 24A, 24B, 25A, 25B, 26A, 26B, 27A, 27B, 28, and 29, the process is added to observe obvious deformity, joint space narrowing 40, a slight crush of a caput 41, and focal necrosis 42 in a band pattern area to be seen in an MR image and characteristic to avascular necrosis of the femoral head more distinctively than FIG. 25B in particular.

ANF (avascular necrosis of the femoral head) is a disease due to circulatory deficits generated by a certain cause in the femoral head, causing necrosis of bone tissue in the bone head. ANF is classified into symptomatic avascular necrosis of the femoral head with precise causes of necrosis such as trauma and caisson disease, and idiopathic avascular necrosis of the femoral head without precise causes. Causes to generate ANF include a post trauma state such as dislocation of the hip and a fracture of the neck of femur, Perthes disease, caisson disease, radiation irradiation, oral administration of a steroid agent, and alcohol intake in a large amount, but the causes are unspecified and unknown in many cases. Diagnosis is made by the simple X-ray examination with classification of four disease stages.

First stage: A stage without abnormality observed in the simple X-ray examination.

Second stage: A stage with a slight degree of necrosis in the femoral head and a narrow bony sclerosis/consolidation observed.

Third stage: A stage with a progressive range of necrosis in the femoral head and a crushed image of the bone head observed while a joint fissure gap is sustained.

Forth stage: A stage with broken acetabulum and joint space narrowing in a state similar to osteoarthritis of the hip.

These classifications can be used as a good index for treatment selection after diagnosis. Diagnosis is relatively easy in the simple X-ray examination. However, abnormal findings are not observed by the simple X-ray examination in an early case (first term), so that bone scintigraphy and MRI or the like are required.

Concrete setting values in each of the processes according to the present invention are shown in the case 1 through the case 6 in the first through sixth embodiments. For the image processing, image processing software Photo Deluxe (product name) made by Adobe Systems Incorporated was used. In the case 1 through the case 6, detailed values of the contrast process are summarized as shown in a table 1 below when the image processing was applied according to the present invention.

TABLE 1

| Case | Fracture area Days (W) | Appearance scale (%) | Contrast process B: Brightness | Contrast process C: Contrast |
|---|---|---|---|---|
| 1 | Separation of the epiphyseal line at the lower ends of the tibia—1 | — | — | — |
| 2 | Fracture of the carpal scaphoid—1 | 28 | −19 | 15 |
|   | Fracture of the carpal scaphoid—2 | 28 | −2 | 30 |
|   | Fracture of the carpal scaphoid—3 | 28 | −25 | 18 |
| 3 | Fracture of the fibular head—1 | 18 | −11 | 7 |
|   | Fracture of the fibular head—2 | 18 | −17 | 10 |
|   | Fracture of the fibular head—3 | 18 | −14 | 5 |
| 4 | Osteoarthritis of the hip: R | 23 | −74 | 18 |
|   | Osteoarthritis of the hip: L | 23 | −52 | 16 |
| 5 | Osteoarthritis of the knee | 20 | −51 | 29 |
| 6 | Front image of avascular necrosis of the femoral head: R | 15 | −32 | 18 |
|   | Front image of avascular necrosis of the femoral head: L | 15 | −6 | 45 |
|   | Lauenstein image of avascular necrosis of the femoral head: R | 15 | −10 | 30 |
|   | Lauenstein image of avascular necrosis of the femoral head: L | 15 | −11 | 13 |
|   | Axial image of avascular necrosis of the femoral head: L | 15 | −52 | 5 |

In the above case 1 through the case 6, respective detailed values of the emboss process and the light irradiation process are summarized as shown in a table 2 below when the image processing was applied according to the present invention.

TABLE 2

| | | Emboss process | | |
|---|---|---|---|---|
| Case | Fracture area Days (W) | A: angle (°) | H: height (pixel) | M: applicable capacity (%) |
| 1 | Separation of the epiphyseal line at the lower ends of the tibia—1 | — | — | — |
| 2 | Fracture of the carpal scaphoid—1 | −90 | 8 | 220 |
| | Fracture of the carpal scaphoid—2 | −90 | 8 | 220 |
| | Fracture of the carpal scaphoid—3 | −90 | 8 | 220 |
| 3 | Fracture of the fibular head—1 | −170 | 10 | 500 |
| | Fracture of the fibular head—2 | −170 | 10 | 500 |
| | Fracture of the fibular head—3 | −170 | 10 | 500 |
| 4 | Osteoarthritis of the hip: R | −30 | 10 | 400 |
| | Osteoarthritis of the hip: L | −150 | 10 | 400 |
| 5 | Osteoarthritis of the knee | −50 | 10 | 280 |
| 6 | Front image of avascular necrosis of the femoral head: R | 17 | 8 | 400 |
| | Front image of avascular necrosis of the femoral head: L | 163 | 8 | 400 |
| | Lauenstein image of avascular necrosis of the femoral head: R | 17 | 8 | 400 |
| | Lauenstein image of avascular necrosis of the femoral head: L | 163 | 8 | 400 |
| | Axial image of avascular necrosis of the femoral head: L | 163 | 8 | 400 |

In the above case 1, a shallow relief process was performed in place of the contrast process and the emboss process according to the present invention, and detailed values thereof are summarized as shown in a table 3 below. The shallow relief process uses a shade difference of an X-ray image for a three-dimensional effect as if an image is provided with relief, and a remarkable effect is expected by this process as shown in FIGS. 18 and 19. This is considered to theoretically confirm preciseness to allow correct diagnosis of a fracture or the like by forming shade and a boundary line in an area with a suspected fracture for using the shade and output of the boundary line owing to the emboss process and the light irradiation process. The reason to apply this process exclusively to the separation of the epiphyseal line at the lower ends of the tibia in the case 1 is to allow remarkable observation of an effect of the shallow relief process in this case.

TABLE 3

| | | Shallow belief process | | |
|---|---|---|---|---|
| Case | Fracture area days(W) | Details | Smoothness | Irradiation direction |
| 1 | Separation of the epiphyseal line at the lower ends of the tibia—1 | 14 | 5 | Downward |
| 2 | Fracture of the carpal scaphoid—1 | — | — | — |
| | Fracture of the carpal scaphoid—2 | — | — | — |
| | Fracture of the carpal scaphoid—3 | — | — | — |
| 3 | Fracture of the fibular head—1 | — | — | — |
| | Fracture of the fibular head—2 | — | — | — |
| | Fracture of the fibular head—3 | — | — | — |
| 4 | Osteoarthritis of the hip: R | — | — | — |
| | Osteoarthritis of the hip: L | — | — | — |
| 5 | Osteoarthritis of the knee | — | — | — |
| 6 | Front image of avascular necrosis of the femoral head: R | — | — | — |
| | Front image of avascular necrosis of the femoral head: L | — | — | — |
| | Lauenstein image of avascular necrosis of the femoral head: R | — | — | — |
| | Lauenstein image of avascular necrosis of the femoral head: L | — | — | — |
| | Axial image of avascular necrosis of the femoral head: L | — | — | — |

INDUSTRIAL APPLICABILITY

According to the present invention, existence of unclear orthopedic and oral surgery diseases is observed more distinctively in an X-ray image, in which any medical workers with basic medical knowledge can determine existence of these diseases. This technique is not limited to orthopedic and oral surgery diseases, being considered to be extremely beneficial in industry with a significant possibility of utilization in a field such as a nondestructive inspection.

The invention claimed is:

1. A system for processing simple X-ray images for diagnosing orthopedic diseases and diseases that are subject to oral surgery, the X-ray image processing system comprising:
   a computer;
   an X-ray image provision means for capturing simple two dimensional X-ray images as pixel data into the computer;
   means for carrying out a contrast adjustment process between a dark colored part and a bright colored part on a target X-ray image captured into the computer, wherein the pixel data of the X-ray image has a predetermined contrast, and a height is added to the two dimensional plane X-ray image;
   a light irradiation means for irradiating light to an outline area raised from an arbitrary angle so as to cause the area to be seemingly floated from the surface;
   an emboss-processing means for carrying out an embossing process on the contrast-adjustment processed X-ray image, by using an emboss filter to arithmetically convert gradation values in each of the pixel data of the target X-ray image to bring the image into a three-dimensional state;
   a shading means for adding light irradiated from a given angle and shade to the pixel data of the emboss-processed X-ray image, so that depth is added to height, thereby obtaining a visually three-dimensional floated image;
   image management means for storing and managing the emboss- and shading-processed X-ray image; and
   image output means, responsive to said image management means, for outputting the visually three-dimensional floated image on a display monitor or to a printer.

2. The system for processing simple X-ray images as claimed in claim 1 for diagnosing orthopedic diseases and diseases that are subject to oral surgery, wherein the emboss-processing means can exclusively make contribution to improvement of the X-ray image without executing the contrast process.

3. The X-ray image processing system as claimed in claim 1, wherein the X-ray image provision means is either a digital X-ray camera or a computed radiography scanner connected to the computer.

4. A method for processing simple x-ray image for diagnosing orthopedics diseases and diseases that are subject to oral surgery, the x-ray image processing method comprising:

an X-ray image provision step of capturing simple two dimensional X-ray images as pixel data into a computer;

a step of applying a contrast adjustment process between a dark colored part and a bright colored part on a target X-ray image captured into the computer, wherein the pixel data of the X-ray image has a predetermined contrast, and a height is added to the two dimensional plane X-ray image;

a light irradiation step of irradiating light to an outline area raised from an arbitrary angle so as to cause the area to be seemingly floated from the surface;

an embossing step of carrying out an embossing process on the contrast-adjustment processed x-ray image captured in the image provision step using an emboss filter to arithmetically convert gradation values in each of the pixel data of the target X-ray image to bring the image into a three-dimensional state;

a shading step of adding light irradiated from a given angle and shade to the pixel data of the x-ray image processed in the embossing step so that depth is added to height, thereby obtaining a visually three dimensional floated image;

a step of storing and managing the x-ray image processed in the shading step; and a step of outputting the visually three-dimensional floated image on a display or a printer.

5. The X-ray image processing system as claimed in claim 1, further comprising:

input means for inputting individual subjects' examination records;

storing means for storing the input examination records as individual examination histories;

means for collating the stored examination records with the examination records input by the input means;

means for determining whether an examination in an input record is a reexamination; and means for, if the determining means determines the examination is a reexamination, retrieving the previous examination result automatically, and displaying the previous examination result.

6. The X-ray image processing system as claimed in claim 2, further comprising:

input means for inputting individual subjects' examination records;

storing means for storing the input examination records as individual examination histories;

means for collating the stored examination records with the examination records input by the input means;

means for determining whether an examination in an input record is a reexamination; and means for, if the determining means determines the examination is a reexamination, retrieving the previous examination result automatically, and displaying the previous examination result.

7. A non-transitory computer readable storage medium on which is recorded a program executable by a computer to enable the computer to carry out the X-ray image processing method according to claim 4.

* * * * *